US009434975B2

(12) United States Patent
Roscoe et al.

(10) Patent No.: US 9,434,975 B2
(45) Date of Patent: Sep. 6, 2016

(54) FLUOROGENIC OR FLUOROPHORIC COMPOUNDS AND USES THEREOF

(75) Inventors: Stephen B. Roscoe, Woodbury, MN (US); Shih-Hung Chou, Maplewood, MN (US); Stephanie J. Moeller, Stillwater, MN (US); Jesse D. Miller, Hudson, WI (US); Kurt J. Halverson, Lake Elmo, MN (US); Jason W. Bjork, Newport, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 62 days.

(21) Appl. No.: 14/008,905

(22) PCT Filed: Mar. 5, 2012

(86) PCT No.: PCT/US2012/027698
§ 371 (c)(1),
(2), (4) Date: Oct. 14, 2013

(87) PCT Pub. No.: WO2012/134724
PCT Pub. Date: Oct. 4, 2012

(65) Prior Publication Data
US 2014/0186878 A1 Jul. 3, 2014

Related U.S. Application Data

(60) Provisional application No. 61/469,355, filed on Mar. 30, 2011.

(51) Int. Cl.
*C12Q 1/04* (2006.01)
*C07D 311/16* (2006.01)
*C07D 405/04* (2006.01)
*C07D 409/04* (2006.01)
*C07H 17/075* (2006.01)
*G01N 33/52* (2006.01)
*G01N 33/58* (2006.01)

(52) U.S. Cl.
CPC ............. *C12Q 1/04* (2013.01); *C07D 311/16* (2013.01); *C07D 405/04* (2013.01); *C07D 409/04* (2013.01); *C07H 17/075* (2013.01); *C12Q 1/045* (2013.01); *G01N 33/525* (2013.01); *G01N 33/582* (2013.01)

(58) Field of Classification Search
CPC ...... C12Q 1/04; C12Q 1/045; G01N 33/525; G01N 33/582; C07H 17/075; C07D 405/04; C07D 409/04; C07D 311/16
See application file for complete search history.

(56) References Cited

U.S. PATENT DOCUMENTS

| | | | |
|---|---|---|---|
| 4,201,783 A * | 5/1980 | Briet et al. | ............ 514/281 |
| 4,565,783 A | 1/1986 | Hansen | |
| 5,089,413 A | 2/1992 | Nelson | |
| 5,681,712 A | 10/1997 | Nelson | |
| 5,830,912 A * | 11/1998 | Gee et al. | ............ 514/457 |
| 5,958,782 A | 9/1999 | Bentsen | |
| 6,566,508 B2 | 5/2003 | Bentsen | |
| 6,703,120 B1 | 3/2004 | Ko | |
| 2011/0318772 A1* | 12/2011 | Diwu et al. | ............ 435/29 |
| 2012/0094327 A1 | 4/2012 | Young | |
| 2012/0301911 A1 | 11/2012 | Roscoe | |

FOREIGN PATENT DOCUMENTS

WO    WO 2012/012104     1/2012

OTHER PUBLICATIONS

Chilvers et. al., "Synthesis and evaluation of novel fluorogenic substrates for the detection of bacterial β-galactosidase", *J. Appl. Microbio.*, vol. 91, (2001) pp. 1118-1130.
Copeland, et al., "The Preparation and Reaction of 2-Benzimidazolecarboxylic Acid and 2-Benzimid-azoleacetic Acid", *Journal of the American Chemical Society*, (1943), vol. 65, pp. 1072-1075.
Elnagdi et. al., "Synthesis of Some Coumarin Derivatives as Potential Laser Dyes", *Journal of Chemical Research (S)*, (1997) 44-45.
Gee et al.,"Fluorogenic Substrates Based on Fluorinated Umbelliferones for Continuous Assays of Phosphatases and β-Galactosidases" *Analytical Biochemistry*, vol. 273, (1999) pp. 41-48.
Guo et al, "Synthesis and study on fluorescent properties of 3-pyridylcoumarins" *Huaxue Shiji*, 32(8), (2010) 673-676.
Kangyu, et al., "Novel Coumarin-based Fluorescent Probe for Selective Detection of Bisulfite Anion in Water", *Chin. J. Chem.*, vol. 28, (2010) pp. 55-60.
Koller, et al., "Syntheses and Spectral Properties of Longwave Absorbing and Fluorescing Substrates for the Direct and Continuous Kinetic Assay of Carboxylesterases, Phosphatases, and Sulfatases", *Monatshefte fur Chemie*, vol. 116, (1985) pp. 65-75.
Song, et al., "Synthesis and Characterization of Coumarin Fluorescent Compounds", Fine Chemcials, vol. 26, No. 6, (2009) pp.
Sun, et al., "Synthesis of Fluorinated Fluoresceins", *J. Org Chem.*, vol. 62, (1997) pp. 6469-6475.
Sun, et al., "Synthesis of Novel Fluorinated Coumarins: Excellent UV-Light Excitable Fluorescent Dyes", *Bioorg. & Med. Chem. Lett.*, vol. 8, (1998) pp. 3107-3110.
Yang et. al., "A Novel Fluorogenic Coumarin Substrate for Monitoring Acid Phosphtase Activity at Low pH Environment", *Current Chemical Genomics*, vol. 2, (2008) pp. 48-40.

* cited by examiner

*Primary Examiner* — Sudhakar Katakam
(74) *Attorney, Agent, or Firm* — 3M Innovative Properties Company; Eric E. Silverman

(57) ABSTRACT

Compounds are provided that are either fluorogenic or fluorophoric. Compositions and articles that include the compounds are also provided. Additionally, methods of detecting a microorganism using the compounds are provided. The compounds are fluorinated and can be used advantageously under acidic conditions.

17 Claims, 4 Drawing Sheets

FLUOROGENIC OR FLUOROPHORIC COMPOUNDS AND USES THEREOF

CROSS REFERENCE TO RELATED APPLICATIONS

This application is a national stage filing under 35 U.S.C. 371 of PCT/US2012/027698, filed Mar. 5, 2012, which claims priority to U.S. Provisional Patent Application No. 61/469,355, filed Mar. 30, 2011, the disclosures of which are incorporated by reference in their entirety herein.

FIELD

The present disclosure relates to fluorogenic and fluorophoric compounds, compositions and articles that include these compounds, methods of making these compounds, and methods of detecting microorganisms utilizing these compounds.

BACKGROUND

Various 7-hydroxycoumarin-based compounds (also called umbelliferones) and their derivatives have been used as fluorescence indicators for enzymatic activity. The umbelliferones are fluorescent but when the 7-hydroxy group is functionalized with an enzyme-labile group, the fluorescence of the resulting compound is quenched. When contacted with an appropriate enzyme, the enzyme-labile group can be released through hydrolysis resulting in the reformation of the 7-hydroxy group and restoration of fluorescence.

Some known fluorescent indicators include those described, for example, in U.S. Pat. No. 5,830,912 (Gee et al.), U.S. Pat. No. 6,566,508 (Bentsen et al.), in the article by Gee et al., *Analytical Biochemistry*, 273, 41-48 (1999), and in the article by Guo et al, *Huaxue Shiji*, 32(8), 673-676 (2010).

One example fluorescent indicator is 4-methylumbelliferone glucuronide, which is referred to as 4-MUG. When exposed to a microorganism such as coliform, the non-fluorescent 4-MUG is transformed to the fluorescent compound 4-methylumbelliferone, which is referred to as 4-MU. When used as a fluorescent indicator for enzymatic activity, the pH of the sample typically must be basic to maximize the fluorescent signal of 4-MU. That is, compounds such as 4-MU can exist in both an acid and basic form with the basic form having significantly greater fluorescence at the wavelength of interest (e.g., the wavelength of maximum absorption, emission, or both).

SUMMARY

Compounds that are capable of fluorescence under acidic conditions are needed for the detection of various microorganisms. Compounds are provided that are either (a) fluorescent under acidic conditions or (b) fluorescent under acidic conditions after exposure to an enzyme that converts an enzyme-labile group to a hydroxyl group. Compositions and articles that include the compounds are also provided. Additionally, methods of making the compounds and methods of detecting a microorganism using the compounds are provided.

In a first aspect, compounds of Formula (I) are provided.

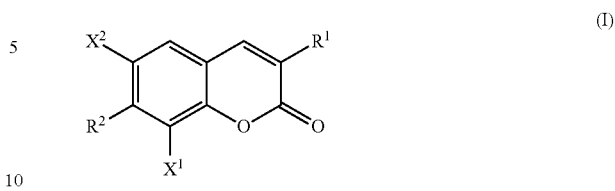

In Formula (I), $R^1$ is —(CO)—$OR^3$, —(CO)—$NR^4R^5$, heterocyclic group, aryl, aralkyl, or cyano. Group $R^3$ is alkyl, alkenyl, aryl, or aralkyl. Groups $R^4$ and $R^5$ are each independently hydrogen, alkyl, aryl, or aralkyl. Group $R^2$ is hydroxyl or an enzyme-labile group. Either (a) $X^1$ is hydrogen and $X^2$ is fluoro or (b) $X^1$ is fluoro and $X^2$ is hydrogen.

In a second aspect, a method of preparing a compound of Formula (Ib) is provided.

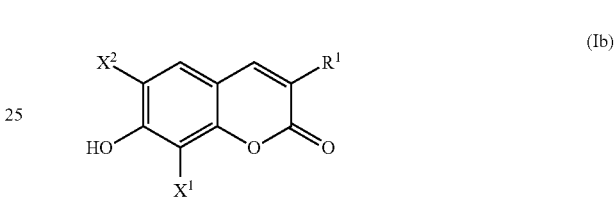

In Formula (Ib), $R^1$ is —(CO)—$OR^3$, —(CO)—$NR^4R^5$, heterocyclic group, aryl, aralkyl, or cyano. Group $R^3$ is alkyl, alkenyl, aryl, or aralkyl. Groups $R^4$ and $R^5$ are each independently hydrogen, alkyl, aryl, or aralkyl. Either (a) $X^1$ is hydrogen and $X^2$ is fluoro or (b) $X^1$ is fluoro and $X^2$ is hydrogen. The method involves the direct fluorination of 2,4-dihydroxybenzaldehyde with a fluorinating agent to form a fluorinated intermediate that is 3-fluoro-2,4-dihydroxybenzaldehyde, 5-fluoro-2,4-dihydroxybenzaldehyde, or a mixture thereof. The fluorinated intermediate is then reacted with a compound of Formula (III)

$$R^1—CH_2—R^{20} \quad \text{(III)}$$

to form the compound of Formula (Ib). In Formula (III), group $R^1$ is the same as defined for Formula (Ib) and group $R^{20}$ is cyano, a carboxyl group (—COOH), or a group of formula —$COOR^1$.

In a third aspect, a composition is provided that includes a compound of Formula (I) and a water-miscible organic solvent.

In a fourth aspect, an article is provided that includes a first layer that is a support layer and a second layer that contains a compound of Formula (I). The second layer is adjacent to the support layer.

In a fifth aspect, a method of detecting a microorganism is provided. The method includes providing a fluorogenic compound of Formula (Ia).

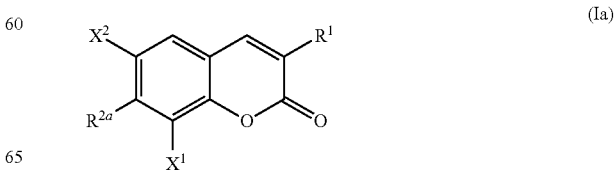

In Formula (Ia), $R^1$ is —(CO)—$OR^3$, —(CO)—$NR^4R^5$, heterocyclic group, aryl, aralkyl, or cyano. Group $R^3$ is alkyl, alkenyl, aryl, or aralkyl. Group $R^4$ and $R^5$ are each independently hydrogen, alkyl, aryl, or aralkyl. Group $R^{2a}$ is an enzyme-labile group. Either (a) $X^1$ is hydrogen and $X^2$ is fluoro or (b) $X^1$ is fluoro and $X^2$ is hydrogen. The method further includes incubating a test sample with the fluorogenic compound of Formula (Ia), wherein the test sample contains an enzyme from the microorganism and the enzyme hydrolyzes group $R^{2a}$ resulting in the formation of a fluorophoric compound of Formula (Ib).

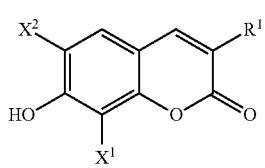
(Ib)

The method still further includes exciting the fluorophoric compound of Formula (Ib) with a first wavelength of light and detecting light emitted at a second wavelength of light that is longer than first wavelength of light.

DETAILED DESCRIPTION

Figure 1A:
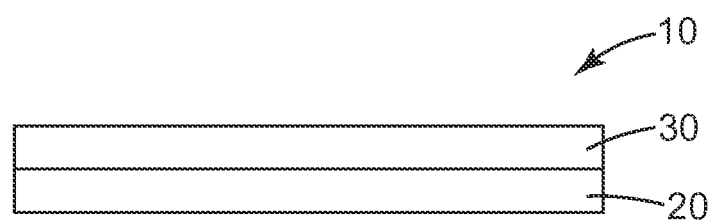
FIGS. 1a and 1b are both example schematic diagrams of articles that can include a compound of Formula (I).

Compounds are provided that are either fluorogenic or fluorophoric. Compositions and articles that include the compounds are also provided. Additionally, methods of making these compounds and methods of detecting microorganisms using the compounds are provided. The compounds are fluorinated and can be used advantageously under acidic conditions. The fluorinated compounds often have increased lipophilicity compared to analogous compounds without fluorine atoms.

The recitation of any numerical range by endpoints is meant to include the endpoints of the range, all numbers within the range, and any narrower range within the stated range.

The term "a", "an", and "the" are used interchangeably with "at least one" to mean one or more of the elements being described.

The term "and/or" means either or both. For example, the expression "A and/or B" means A, B, or a combination of A and B.

The term "alkyl" refers to a monovalent group that is a radical of an alkane and includes groups that are linear, branched, cyclic, bicyclic, or a combination thereof. The alkyl group typically has 1 to 30 carbon atoms. In some embodiments, the alkyl group contains 1 to 20 carbon atoms, 1 to 10 carbon atoms, 1 to 6 carbon atoms, 1 to 4 carbon atoms, or 1 to 3 carbon atoms. It is understood that a branched alkyl can have a minimum of 3 carbon atoms and a cyclic alkyl group can have a minimum of 3 carbon atoms.

The term "alkylene" refers to a divalent group that is a radical of an alkane and includes groups that are linear, branched, cyclic, bicyclic, or a combination thereof. The alkylene group typically has 1 to 30 or 2 to 30 carbon atoms. In some embodiments, the alkylene group has 2 to 20 carbon atoms, 2 to 10 carbon atoms, 2 to 6 carbon atoms, or 2 to 4 carbon atoms.

The term "alkenyl" refers to a monovalent group that is a radical of an alkylene having at least one carbon-carbon double bond and includes groups that are linear, branched, cyclic, bicyclic, or a combination thereof. The alkenyl group typically has 2 to 30 carbon atoms. In some embodiments, the alkenyl group contains 2 to 20 carbon atoms, 2 to 12 carbon atoms, 2 to 10 carbon atoms, or 2 to 6 carbon atoms.

The term "aryl" refers to a monovalent group that is aromatic and carbocyclic. The aryl can have one or more carbocyclic rings that are fused to the aromatic ring. Any additional rings can be unsaturated, partially saturated, or saturated. Aryl groups often have 6 to 20 carbon atoms, 6 to 18 carbon atoms, 6 to 16 carbon atoms, 6 to 12 carbon atoms, or 6 to 10 carbon atoms.

The term "arylene" refers to a divalent group that is aromatic and carbocyclic. The arylene can have one or more carbocyclic rings that are fused to the aromatic ring. Any additional rings can be unsaturated, partially saturated, or saturated. Arylene groups often have 6 to 20 carbon atoms, 6 to 18 carbon atoms, 6 to 16 carbon atoms, 6 to 12 carbon atoms, or 6 to 10 carbon atoms.

The term "aralkyl" refers to a monovalent group that is an alkyl group substituted with an aryl group. Aralkyl groups often have an alkyl portion with 1 to 10 carbon atoms, 1 to 6 carbon atoms, or 1 to 4 carbon atoms and an aryl portion with 6 to 20 carbon atoms, 6 to 18 carbon atoms, 6 to 16 carbon atoms, 6 to 12 carbon atoms, or 6 to 10 carbon atoms.

The term "aralkylene" refers to a divalent group that is an alkylene group substituted with an aryl group. Aralkylene groups often have an alkyl portion with 1 to 10 carbon atoms, 1 to 6 carbon atoms, or 1 to 4 carbon atoms and an aryl portion with 6 to 20 carbon atoms, 6 to 18 carbon atoms, 6 to 16 carbon atoms, 6 to 12 carbon atoms, or 6 to 10 carbon atoms.

The term "carbonyl" refers to a divalent group of formula —(CO)— where the carbon is attached to the oxygen with a double bond.

The term "cyano" refers to the monovalent group —C≡N.

The term "heterocyclic group" refers to a monovalent group having a first ring with 3 to 7 ring members wherein at least one ring member is a heteroatom and wherein at least one ring member is carbon. Suitable heteroatoms are selected from oxygen, sulfur, or nitrogen. All ring members that are not heteroatoms are carbon. The first ring can be saturated, partially unsaturated, or unsaturated. The first ring optionally can be fused to one or more carbocyclic or heterocyclic rings. The heterocyclic group typically has 1 to 5 heteroatoms and 1 to 15 carbon atoms, 1 to 4 heteroatoms and 1 to 10 carbon atoms, 1 to 3 heteroatoms and 1 to 10 carbon atoms, or 1 to 3 heteroatoms and 1 to 6 carbon atoms. Some example heterocyclic groups have 1 to 3 heteroatoms in a five member ring. Other example heterocyclic groups have 1 to 3 heteroatoms in a five member ring that is fused to a second ring that is carbocyclic and saturated, partially unsaturated, or unsaturated. For example, a five member ring with 1 to 3 heteroatoms can be fused to a benzene ring.

The term "nitro" refer to the monovalent group —$NO_2$.

The term "fluorogenic" refers to a compound that is not fluorescent or is only weakly fluorescent but that can be converted to a fluorophoric compound that is fluorescent. The fluorescence can be in any region of the electromagnetic spectrum but is often in the ultraviolet, visible, or infrared region.

The term "fluorophoric" refers to a compound that is fluorescent. The fluorescence can be in any region of the electromagnetic spectrum but is often in the ultraviolet, visible, or infrared region.

The term "lipophilicity" refers to the ability of a compound to partition into an organic phase. Lipophilicity can be characterized, for example, by placing a compound of interest in a mixture of a nonpolar, organic solvent (e.g., octanol) and water. The lipophilicity index is a ratio of the concentration of the compound of interest in the organic phase to the concentration of the compound of interest in the aqueous phase. The higher this ratio is, the greater the lipophilicity of the compound.

Compounds such as 7-hydroxycoumarins (i.e., umbelliferones) are known fluorescent indicators. That is, these compounds are fluorophoric compounds. When the 7-hydroxyl group on the coumarin-based compound is replaced with an enzyme-labile group such as a sugar group, phosphate group, or sulfonate group, the fluorescence of the compound is typically quenched. That is, these compounds with the enzyme-labile group are fluorogenic compounds. Reaction of an appropriate enzyme can hydrolyze the enzyme-labile group and convert the fluorogenic compounds into fluorophoric compounds. The enzyme-labile group is converted to a hydroxyl group.

The coumarin-based compounds with an enzyme-labile group can be used to detect the presence of certain enzymes that are indicative of the presence of certain microorganisms. If a sample under analysis contains an enzyme that can hydrolyze (e.g., cleave) the enzyme-labile group of the fluorogenic compound, the resulting fluorophoric compound with a 7-hydroxyl group can fluoresce. To be effective as fluorescent indicators, the pH of the sample under analysis often has to be alkaline (preferably pH 9 to 10). This pH adjustment is needed because the 7-hydroxyl group of the fluorophoric compounds can exist in either an acidic form or basic form. The maximum fluorescent signal is typically obtained for the basic form.

Furthermore, many microorganisms (e.g., E. coli) tend to generate acids as part of their metabolic processes. The pH of a sample containing such microorganisms tends to become more acidic over time. This pH drop can cause the fluorescence intensity to diminish over time, can cause a misleading low fluorescent signal, or both. In extreme cases, the fluorescent signal can be reduced to a level comparable to the background signal. Thus, fluorescent indicators are needed that can be used in an acidic environment and that can provide a stable fluorescent signal in an acidic environment.

Difluorinated coumarin-based compounds are know that can have good fluorescent stability in an acidic range such as in a range of pH 5 to 7. However, the strong electron-withdrawing character of the two fluorine atoms can be sufficient to weaken the bond between the coumarin core and the enzyme-labile group. This is evidenced by the pKas for 6,8-difluoro-4-methyl-7-hydroxycoumarin and 6,8-difluoro-3-ethylcarboxylate-7-hydroxycoumarin being 4.2 and 3.8 respectively (see *Bioorg. and Med. Chem. Lett.*, 8, 3107-3110 (1998)).

To overcome the difficulties with the known coumarin-based fluorescent indicators, the compounds described herein have a single fluorine group. They tend to have stable fluorescent signals even when used in an acidic environment. Additionally, they tend to be less susceptible to hydrolysis of the enzyme-labile group in the absence of an enzyme.

An additional problem with some known coumarin-based fluorogenic compounds is that the maximum excitation signal is often near 365 nanometers, which is an excitation wavelength that can result in considerable background fluorescence from biological materials. Thus, for samples containing biological materials, it may be desirable to use a fluorescent indicator having a maximum excitation signal closer to about 400 nanometers or even longer. That is, fluorescent indicators with a red shifted fluorescent signal are desired. Many low cost laser diode light sources such as InGaN are suitable for use at wavelengths near 400 nanometers or longer. Some of the compounds provided are suitable for use at excitation wavelengths of 400 nanometers or longer.

The fluorinated compounds provided herein tend to have increased lipophilicity compared to their non-fluorinated counterparts. This increased lipophilicity can be advantageous when using polymeric materials to sequester the compounds. Additionally, increased lipophilicity may facilitate passage of the fluorinated compounds of through cell membranes. This characteristic can be desirable when the target enzyme for the compound is confined within a cell of a microorganism.

In a first aspect, the fluorinated compounds of Formula (I) are provided.

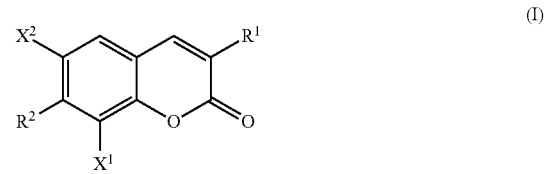

(I)

In Formula (I), group $R^1$ is —(CO)—$OR^3$, —(CO)—$NR^4R^5$, heterocyclic group, aryl, aralkyl, or cyano. Group $R^3$ is alkyl, alkenyl, aryl, or aralkyl. Groups $R^4$ and $R^5$ are each independently hydrogen, alkyl, aryl, or aralkyl. Group $R^2$ is hydroxyl or an enzyme-labile group. Either (a) $X^1$ is hydrogen and $X^2$ is fluoro or (b) $X^1$ is fluoro and $X^2$ is hydrogen.

In some embodiments, the group $R^1$ is of formula —(CO)—O—$R^3$ where $R^3$ is an alkyl, alkenyl, aryl, or aralkyl. Suitable alkyl groups for $R^3$ often have 1 to 10 carbon atoms, 1 to 6 carbon atoms, 1 to 4 carbon atoms, or 1 to 3 carbon atoms. Suitable alkenyl groups for $R^3$ often have 2 to 12 carbon atoms, 2 to 10 carbon atoms, or 2 to 6 carbon atoms. Suitable aryl groups often have 6 to 12 carbon atoms and suitable aralkyl groups often have 7 to 12 carbon atoms. For example, the aryl group can be phenyl and the aralkyl group can have an alkyl group with 1 to 6 carbon atoms substituted with phenyl. Some specific $R^1$ groups include, but are not limited to, ethyl carboxylate (—(CO)—O—CH$_2$CH$_3$) and phenyl carboxylate (—(CO)—O—C$_6$H$_5$).

In other embodiments, the group $R^1$ is of formula —(CO)—NR$^4$R$^5$ where $R^4$ and $R^5$ are each independently hydrogen, alkyl, aryl, or aralkyl. Suitable alkyl groups for $R^4$ and/or $R^5$ often have 1 to 10 carbon atoms, 1 to 6 carbon atoms, 1 to 4 carbon atoms, or 1 to 3 carbon atoms. Suitable aryl groups for $R^4$ and/or $R^5$ often have 6 to 12 carbon atoms. The aryl group can be phenyl. Suitable aralkyl groups for $R^4$ and/or $R^5$ often have 7 to 12 carbon atoms. The aralkyl group often has an alkyl with 1 to 6 carbon atoms that is substituted with a phenyl.

In still other embodiments, the group $R^1$ is a heterocyclic group. Any suitable heterocyclic group having at least one heterocyclic ring (i.e., a first heterocyclic ring) can be used. The first heterocyclic ring includes at least one heteroatom ring member with the remaining ring members being carbon. Each heteroatom ring member is selected from oxygen, sulfur, or nitrogen. The first heterocyclic ring often has 3 to 7 ring members and can be fused to additional rings that are either carbocyclic or heterocyclic.

Some heterocyclic groups have a first heterocyclic ring with 3 or 4 ring members. Examples of heterocyclic groups with 3 ring members include, but are not limited to, aziridinyl, oxiranyl, and thiiranyl. Examples of heterocyclic groups with 4 ring members include, but are not limited to, azetidinyl, oxetanyl, and thietanyl.

Some heterocyclic groups have a first heterocyclic ring with 5 ring members. Examples of saturated heterocyclic groups with a single heteroatom include, but are not limited to, pyrrolidinyl, oxolanyl, and tetrahydrothiophenyl. Examples of partially unsaturated or unsaturated heterocyclic groups with a single heteroatom include, but are not limited to, pyrrolyl, furanyl, and thienyl. Examples of saturated heterocyclic rings with more than one heteroatom include, but are not limited to, dioxolanyl and trioxanyl. Examples of partially unsaturated or unsaturated heterocyclic groups with more than one heteroatom include, but are not limited to, imidazolyl, oxazolyl, triazolyl, tetrazolyl, thiazolyl, isoxazolyl, isothiazolyl, and oxadiazolyl. Example heterocyclic groups with a first heterocyclic ring with 5 members fused to a carbocyclic ring such as a benzene ring include, but are not limited to, indolyl, isoindolyl, benzofuranyl, benzothienyl, benzimidazolyl, N-substituted benzimidazolyl, benzthiazolyl, benzoxazolyl, and benzisoxazolyl. Example heterocyclic groups with a first heterocyclic ring with 5 members fused to two carbocyclic rings such as benzene rings or a naphthalene ring system include, but are not limited to, carbazolyl and naphthoxazolyl.

Other heterocyclic groups have a first heterocyclic ring with 6 ring members. Examples of saturated heterocyclic groups with a single heteroatom include, but are not limited to, piperidinyl, tetrahydropyranyl, and thianyl. Examples of partially unsaturated or unsaturated heterocyclic groups with a single heteroatom include, but are not limited to, pyranyl and thiopyranyl. Examples of saturated heterocyclic groups with multiple heteroatoms include, but are not limited to, piperazinyl, morpholinyl, and dioxanyl. Examples of unsaturated or partially unsaturated heterocyclic rings with multiple heteroatoms include, but are not limited to, diazinyl, oxazinyl, thiazinyl, triazinyl, and tetrazinyl. Example heterocyclic groups with a first heterocyclic ring with 6 members fused to a carbocyclic ring such as a benzene ring include, but are not limited to, quinolinyl and isoquinolinyl. Example heterocyclic groups with a first heterocyclic ring with 6 members fused to another heterocyclic ring include, but are not limited to, naphthyridinyl.

Still other heterocyclic groups have seven ring members. Such groups include, but are not limited to, azepinyl, oxepinyl, thiepinyl, diazepinyl, and thiazepinyl.

Any suitable aryl group can be used for $R^1$. Some example aryl groups have 6 to 20 carbon atoms, 6 to 12 carbon atoms, or 6 to 10 carbon atoms. Examples of aryl groups include, but are not limited to, phenyl, naphthyl, acenaphthyl, phenanthrenyl, anthracenyl, pyrenyl, perylenyl, and fluorenyl.

Any suitable aralkyl group can be used for $R^1$. Some example aralkyl groups have an alkyl portion with 1 to 10 carbon atoms, 1 to 6 carbon atoms, or 1 to 4 carbon atoms plus an aryl portion with 6 to 20 carbon atoms, 6 to 12 carbon atoms, or 6 to 10 carbon atoms. One more specific example aralkyl group has an alkyl portion with 1 to 10 carbon atoms, 1 to 6 carbon atoms, or 1 to 4 carbon atoms substituted with a phenyl group.

Aryl, aralkyl, and heterocyclic groups for $R^1$ can optionally be substituted with one or more groups selected from an alkyl, alkoxy, aryl, aralkyl, halo, nitro, cyano, guanidino (i.e., —NH—C(NH$_2$)=NH), —SO$_3$H, —N(R$^6$)$_2$, —R$^7$—(O—R$^7$)—OR$^8$, —(CO)—OR$^9$, or —(CO)—(NR$^{10}$)$_2$. Stated differently, aryl, aralkyl, and heterocyclic groups can be unsubstituted or can be substituted with one or more substituents. Suitable alkyl and alkoxy substituents typically have 1 to 10 carbon atoms, 1 to 6 carbon atoms, or 1 to 4 carbon atoms. Suitable aryl substituents usually have 6 to 12 carbon atoms. Suitable aralkyl substituents usually have 7 to 12 carbon atoms. Suitable halo groups can be fluoro, chloro, or bromo. In substituents of formula —N(R$^6$)$_2$, each $R^6$ independently is hydrogen, alkyl, aryl, or aralkyl. Suitable alkyl groups for $R^6$ typically have 1 to 10 carbon atoms, 1 to 6 carbon atoms, or 1 to 4 carbon atoms. Suitable aryl and aralkyl groups for $R^6$ respectively have 6 to 12 carbon atoms and 7 to 12 carbon atoms. In substituents of formula —R$^7$—(O—R$^7$)—OR$^8$, each group $R^7$ is independently an alkylene, arylene, or aralkylene and group $R^8$ is an alkyl, aryl, or aralkyl. The variable n is an integer in a range of 0 to 10, in a range of 0 to 6, in the range of 0 to 4, or in a range of 0 to 2. Suitable $R^7$ and/or $R^8$ alkylene and alkyl groups typically have 1 to 10 carbon atoms, 1 to 6 carbon atoms, or 1 to 4 carbon atoms. Suitable $R^7$ and/or $R^8$ aryl and aralkyl groups respectively have 6 to 12 and 7 to 12 carbons. In the substituent groups of formula —(CO)—O—R$^9$, the group $R^9$ can be an alkyl, aryl, or aralkyl. Suitable alkyl $R^9$ groups often have 1 to 10 carbon atoms, 1 to 6 carbon atoms, or 1 to 4 carbon atoms. Suitable aryl and aralkyl $R^9$ groups respectively often have 6 to 12 carbon atoms and 7 to 12 carbon atoms. In substituents of formula —(CO)—(NR$^{10}$)$_2$, each group $R^{10}$ independently can be hydrogen, alkyl, aryl, or aralkyl. Suitable $R^{10}$ alkyl groups usually have 1 to 10 carbon atoms, 1 to 6 carbon atoms, or 1 to 4 carbon atoms. Suitable $R^{10}$ aryl groups typically have 6 to 12 carbon atoms and aralkyl groups typically have 7 to 12 carbon atoms.

The $R^2$ group in Formula (I) is a hydroxyl group or an enzyme-labile group. The enzyme-labile groups typically have an oxy group bonded to the aromatic ring. Stated differently, when the enzyme-labile group is hydrolyzed (e.g., cleaved) by action of an enzyme, the reaction product is a hydroxyl group attached to the aromatic ring. Some suitable enzyme-labile groups include, but are not limited to, a sugar group (e.g., a monosaccharide group, disaccharide group, or polysaccharide group), sugar acid group (e.g., a monosaccharide or disaccharide with a carboxyl (—COOH) group), amino sugar group (e.g., a monosaccharide or disaccharide with an amino (—$NH_2$) group), carboxyl-terminated amino acid group, carboxyl-terminated peptide group, ester group, ester-containing group, phosphate group, or sulfate group.

Some suitable enzyme-labile sugar groups for $R^2$ are monovalent groups equal to the residue of a sugar molecule minus hydrogen (i.e., one hydrogen atom). The sugar groups are attached to the aromatic ring in the compounds of Formula (I) through an oxy group. Suitable sugar groups can be monosaccharide groups, disaccharide groups, trisaccharide groups, or polysaccharide groups. Suitable monosaccharide groups include, but are not limited to, alpha-galactopyranosidyl, beta-galactopyranosidyl, alpha-glucopyranosidyl, beta-glucopyranosidyl, alpha-mannopyranosidyl, beta-mannopyranosidyl, alpha-idopyranosidyl, beta-idopyranosidyl, alpha-xylopyranosidyl, beta-xylopyranosidyl, alpha-arabinofuranosidyl, and beta-arabinofuranosidyl. Suitable disaccharide groups include, but are not limited to, beta-cellobiopyranosidyl, beta-lactosyl, 3-O-(alpha-L-fucopyranosyl)-beta-D-galactopyranosyl, 4-O-(alpha-L-fucopyranosyl)-beta-D-galactopyranosyl, beta-xylobiosyl, alpha-maltosyl, beta-maltosyl, trehalosyl, and mannobiosyl. Suitable trisaccharide groups include, but are not limited to, beta-cellotriosyl, beta-gentiotriosyl, and maltotriosyl. Suitable polysaccharide groups include, but are not limited to, beta-cellotetrosidyl and beta-cellopentosidyl.

The enzyme-labile $R^2$ group can also be a sugar acid group that is attached to the aromatic ring in the compounds of Formula (I) through a carbonyloxy group. The sugar acid group is a monovalent group equal to the residue of a sugar acid minus hydrogen (i.e., one hydrogen atom). Suitable sugar acid groups include, but are not limited to, beta-glucuronidyl, alpha-iduronyl, and galacturonyl.

Other enzyme-labile $R^2$ groups are amino sugar groups that are attached to the aromatic ring in the compounds of Formula (I) through an oxy group. The amino sugar group is a monovalent group equal to the residue of an amino sugar minus hydrogen (i.e., one hydrogen atom). Suitable amino sugar groups include, but are not limited to, glucosaminyl, galactosaminyl, chitobiosyl, and chitotriosyl.

Still other enzyme-labile $R^2$ groups are carboxyl-terminated amino acid groups or carboxyl-terminated peptide groups. These groups are attached to the aromatic ring in the compounds of Formula (I) through the carbonyloxy group. Example carboxyl-terminated amino acid groups include, but are not limited to, L-alanyl, L-arginyl, L-aspartyl, L-citrullyl, L-glutamyl, L-glutaminyl, L-glycyl, L-histidyl, L-hydroxyprolyl, L-isoleucyl, L-leucyl, L-lysyl, L-methionyl, L-ornithyl, L-phenylalanyl, L-prolyl, L-seryl, L-threonyl, L-tryptophyl, L-tyrosyl, and L-valyl. Example carboxyl-terminated peptide groups include, but are not limited to, 7-glutaryl-phenylalanyl, L-arginyl-L-arginyl, L-glutaryl-glycyl-arginyl, glycyl-glycyl, glycyl-L-phenylalanyl, glycyl-L-prolyl, and L-seryl-L-tyrosyl, L-prolyl-L-phenylalanyl-arginyl, and N-glutaryl-glycyl-arginyl.

Additional suitable enzyme-labile $R^2$ groups are of formula —O—(CO)—$R^{12}$ where $R^{12}$ is an alkyl, alkyenyl, aryl, or aralkyl. This group is attached to the aromatic ring in the compounds of Formula (I) through an oxy group. Suitable alkyl groups for $R^{12}$ typically have 1 to 20 carbon atoms, 1 to 12 carbon atoms, 1 to 10 carbon atoms, 6 carbon atoms, or 1 to 4 carbon atoms. Suitable alkenyl groups for $R^{12}$ typically have 2 to 20 carbon atoms, 2 to 12 carbon atoms, 2 to 10 carbon atoms, or 2 to 6 carbon atoms. Suitable aryl and aralkyl groups for $R^{12}$ typically have 6 to 12 carbon atoms and 7 to 12 carbon atoms, respectively. Specific $R^2$ groups include, but are not limited to, acetate, propanoate, 2-methylpropanoate, butanoate, 3-methylbutanoate, pentanoate, hexanoate, heptanoate, octanoate, nonanoate, decanoate, undecylate, dodecanoate, tridecanoate, tetradecanoate, pentadecanoate, hexadecanoate, heptadecanoate, octadecanoate, elaidate, oleate, and p-guanidinobenzoate (the aryl is substituted with a guanidino group).

Still other suitable enzyme-labile $R^2$ groups are ester-containing groups of formula —O—$CH_2$—O—(CO)—$R^{13}$ where $R^{13}$ is an alkyl. Suitable alkyl groups for $R^{13}$ usually have 1 to 10 carbon atoms, 1 to 6 carbon atoms, or 1 to 4 carbon atoms. The ester-containing groups are connected to the aromatic ring in the compounds of Formula (I) through an oxy group. Examples include, but are not limited to, acetoxymethoxy, propanoyloxymethoxy, isobutanoyloxymethoxy, and pivaloxymethoxy.

Yet other suitable enzyme-labile $R^2$ groups are ester-containing group of formula —O—$CH_2$—(CO)—$CH_2$—O—(CO)—$R^{14}$ where each $R^{14}$ is an alkyl. Suitable alkyl groups for $R^{14}$ usually have 1 to 10 carbon atoms, 1 to 6 carbon atoms, or 1 to 4 carbon atoms. The ester-containing groups are connected to the aromatic ring in the compounds of Formula (I) through an oxy group. Examples include, but are not limited to 3-(octanoyloxy)-2-oxopropoxy, 3-(decanoyloxy)-2-oxopropoxy, 3-(dodecanoyloxy)-2-oxopropoxy, 3-(butyloxy)-2-oxopropoxy, and 3-(acetyloxy)-2-oxopropoxy.

Other enzyme-labile groups are sulfate groups of formula —O—$SO_2$—($OR^{15}$) or a phosphate group of formula —O—(PO)—($OR^{16}$)$_2$ where each $R^{15}$ and $R^{16}$ independently can each be hydrogen or alkyl. The sulfate groups and phosphate groups are attached to the aromatic ring in the compound of Formula (I) through an oxy group. Suitable alkyl groups for $R^{15}$ and $R^{16}$ often have 1 to 10 carbon atoms, 1 to 6 carbon atoms, or 1 to 4 carbon atoms.

Any aryl or aralkyl groups included in $R^2$ can optionally be substituted with one or more groups selected from an alkyl, alkoxy, aryl, aralkyl, halo, nitro, cyano, guanidino (i.e., —NH—C($NH_2$)=NH), —$SO_3H$, —$N(R^6)_2$, —$R^7$—(O—$R^7)_n$—$OR^8$, —(CO)—$OR^9$, or —(CO)—$(NR^{10})_2$. Stated differently, aryl, or aralkyl groups can be unsubstituted or can be substituted with one or more substituents. Suitable alkyl and alkoxy substituents typically have 1 to 10 carbon atoms, 1 to 6 carbon atoms, or 1 to 4 carbon atoms. Suitable aryl substituents usually have 6 to 12 carbon atoms. Suitable aralkyl substituents usually have 7 to 12 carbon atoms. Suitable halo groups can be fluoro, chloro, or bromo. In substituents of formula —$N(R^6)_2$, each $R^6$ independently is hydrogen, alkyl, aryl, or aralkyl. Suitable alkyl groups for $R^6$ typically have 1 to 10 carbon atoms, 1 to 6 carbon atoms, or 1 to 4 carbon atoms. Suitable aryl and aralkyl groups for $R^6$ respectively have 6 to 12 carbon atoms and 7 to 12 carbon atoms. In substituents of formula —$R^7$—(O—$R^7)_n$—$OR^8$, each group $R^7$ is independently an alkylene, arylene, or aralkylene and group $R^8$ is an alkyl, aryl, or aralkyl. The variable n is an integer in a range of 0 to 10, in a range of 0 to 6, in the range of 0 to 4, or in a range of 0 to 2. Suitable $R^7$ and/or $R^8$ alkylene and alkyl groups typically have 1 to 10 carbon atoms, 1 to 6 carbon atoms, or 1 to 4 carbon atoms. Suitable $R^7$ and/or $R^8$ aryl and aralkyl groups respectively have 6 to 12 and 7 to 12 carbons. In the substituent groups of formula —(CO)—O—R$^9$, the group R$^9$ can be an alkyl, aryl, or aralkyl. Suitable alkyl R$^9$ groups often have 1 to 10 carbon atoms, 1 to 6 carbon atoms, or 1 to 4 carbon atoms. Suitable aryl and aralkyl R$^9$ groups respectively often have 6 to 12 carbon atoms and 7 to 12 carbon atoms. In substituents of formula —(CO)—(NR$^{10}$)$_2$, each group R$^{10}$ independently can be hydrogen, alkyl, aryl, or aralkyl. Suitable R$^{10}$ alkyl groups usually have 1 to 10 carbon atoms, 1 to 6 carbon atoms, or 1 to 4 carbon atoms. Suitable R$^{10}$ aryl groups typically have 6 to 12 carbon atoms and aralkyl groups typically have 7 to 12 carbon atoms.

Specific example compounds of Formula (I) with a hydroxyl R$^2$ group include, but are not limited, 3-ethylcarboxylate-6-fluoro-7-hydroxycoumarin, 3-ethylcarboxylate-8-fluoro-7-hydroxycoumarin, 3-thienyl-6-fluoro-7-hydroxycoumarin, 3-thienyl-8-fluoro-7-hydroxycoumarin, 3-(2-(5-carboxyethylfuranyl))-6-fluoro-7-hydroxycoumarin, 3-(2-(5-carboxyethylfuranyl))-8-fluoro-7-hydroxycoumarin, 3-cyano-6-fluoro-7-hydroxycoumarin, 3-cyano-8-fluoro-7-hydroxycoumarin, 3-benzthiazolyl-6-fluoro-7-hydroxycoumarin, 3-benzthiazolyl-8-fluoro-7-hydroxycoumarin, 3-benzoxazolyl-6-fluoro-7-hydroxycoumarin, 3-benzoxazolyl-8-fluoro-7-hydroxycoumarin, 3-(4-imidazolyl)-6-fluoro-7-hydroxycoumarin, 3-(4-imidazolyl)-8-fluoro-7-hydroxycoumarin, 3-(1-imidazolyl)-6-fluoro-7-hydroxycoumarin, 3-(1-imidazolyl)-8-fluoro-7-hydroxycoumarin, 3-(2-pyrrolyl)-6-fluoro-7-hydroxycoumarin, 3-(2-pyrrolyl)-8-fluoro-7-hydroxycoumarin, 3-benzimidazolyl-6-fluoro-7-hydroxycoumarin, 3-benzimidazolyl-8-fluoro-7-hydroxycoumarin, 3-(1-methylbenzimidazolyl)-6-fluoro-7-hydroxycoumarin, 3-(1-methylbenzimidazolyl)-8-fluoro-7-hydroxycoumarin, 3-benzimidazolyl-6-fluoro-7-hydroxycoumarin, 3-benzimidazolyl-8-fluoro-7-hydroxycoumarin, 3-benzofuranyl-6-fluoro-7-hydroxycoumarin, and 3-benzofuranyl-8-fluoro-7-hydroxycoumarin. Other example compounds have the hydroxy group replaced with an enzyme-labile group that is a sugar group (e.g., a monosaccharide group, disaccharide group, or polysaccharide group), sugar acid group (e.g., a monosaccharide or disaccharide with a carboxyl (—COOH) group), amino sugar group (e.g., a monosaccharide or disaccharide with an amino (—NH$_2$) group), carboxyl-terminated amino acid group, carboxyl-terminated peptide group, ester group, phosphate group, or sulfate group. In some specific examples, the enzyme-labile group is a monosaccharide group such as alpha-galactopyranosidyl, beta-galactopyranosidyl, alpha-glucopyranosidyl, beta-glucopyranosidyl, or beta-glucuronidyl.

The compounds of Formula (Ib), which corresponds to Formula (I) where R$^2$ is a hydroxyl group, can be prepared using any known synthesis method. One particularly useful synthesis method is a direct fluorination method as shown in Reaction Scheme A.

Reaction Scheme A

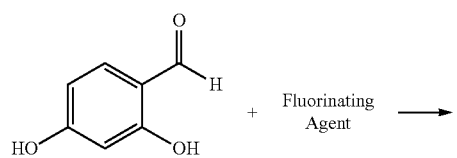

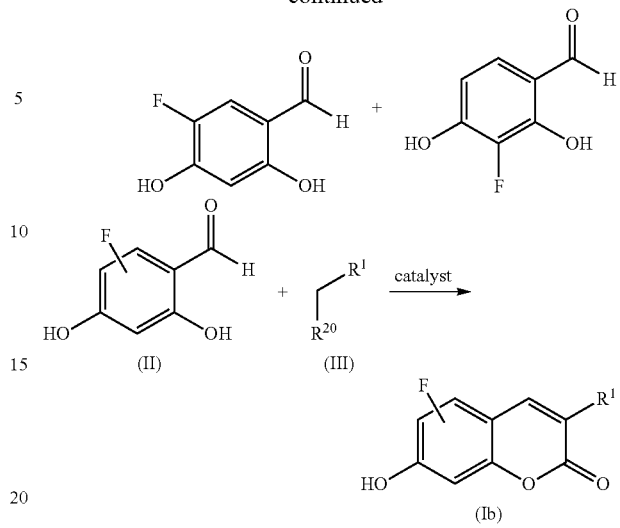

In Reaction Scheme A, 2,4-dihydroxybenzaldehyde is reacted with a fluorinating agent. A fluorinated dihydroxybenzaldehyde intermediate of Formula (II) is prepared initially. The fluorinated dihydroxybenzaldehyde can be 3-fluoro-2,4-dihydroxybenzaldehyde, 5-fluoro-2,4-dihydroxybenzaldehyde, or a mixture thereof. An intermediate compound of Formula (II) is then reacted with a compound of Formula (III) using a Knoevenagel condensation reaction. The compound of Formula (III) has a group R$^1$ that is the same as described above for the compounds of Formula (I) and a group R$^{20}$ that is an electron withdrawing group selected from cyano, a carboxyl group (—COOH), or a group of formula —COOR$^1$. The catalyst used for this second reaction can vary for each particular reaction but can be, for example, ammonium acetate, sodium hydroxide, a mixture of triethylamine and acetic anhydride, or a mixture of morpholine and acetic acid.

Any suitable fluorinating agent can be used in Reaction Scheme A. Some suitable fluorinating agents have a fluorine atom attached to a nitrogen atom (i.e., N—F fluorinating agents). Example N—F fluorinating agents include, but are not limited to, SELECTFLUOR, which is a trade designation of Air Products in Allentown, Pa. for the compound 1-chloromethyl-4-fluoro-1,4-diazabicyclo[2.2.2]octane bis(tetrafluoroborate); ACCUFLUOR, which is a trade designation of Honeywell Organic Fine Chemicals in Seelze, Germany for the compound 1-hydroxy-4-fluoro-1,4-diazobicylo[2.2.2]octane bis(tetrafluoroborate); N-fluorobenzenesulfonimide; 1-fluoropyridinium triflate; and 2,6-dichloro-1-fluoropyridinium tetrafluoroborate. Still other fluorinating agents include tetrabutylammonium hydrogen difluoride, diethylaminosulfur trifluoride, morpholinosulfur trifluoride xenon difluoride, and fluorine.

In one example direct fluorination reaction, the fluorinating agent (e.g., SELECTFLUOR) and 2,4-dihydroxybenzaldehyde can be mixed for several days (e.g., 5 to 10 days) at room temperature (e.g., 20° C. to 25° C.) to form a mixture of 5-fluoro-2,4-dihydroxybenzaldehyde and 3-fluoro-2,4-dihydroxybenzaldehyde in a 5:1 ratio and with a conversion of about 60 percent. The mixture can be further purified by recrystallization.

Example compounds of Formula (III) for use in Reaction Scheme A include, for example, 2-thiophene acetic acid for the preparation of a compound of Formula (Ib) with a thiophenyl group as $R^1$, 2-cyanomethylbenzimidazole for the preparation of a compound of Formula (Ib) with a benzimidazolyl group as $R^1$, and ethyl acetoacetate for the preparation of a compound of Formula (Ib) with a carbonyloxyethyl group (i.e., ethyl carboxylate group) as $R^1$. If desired, the products can be isolated directly by filtration, the reaction solution can be mixed with a non-solvent such as water and the product can be filtered off, or the product can be isolated by solvent extraction.

The product of the second reaction shown in Reaction Scheme A is a compound of Formula (Ib). In many embodiments, the product is a mixture of two fluorinated materials of Formula (Ib-1) and (Ib-2). The product may contain some non-fluorinated material of Formula (IV).

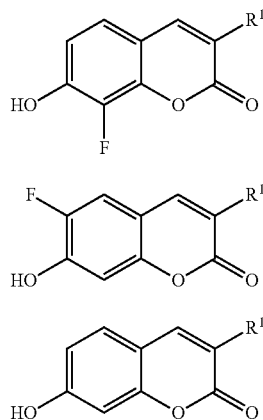

The fluorinated materials (i.e., compounds of Formulas (Ib-1) and (Ib-2)) can be separated from the non-fluorinated material (i.e., compounds of Formula (IV)) using, for example, various chromatographic methods. The resulting purified mixture often contains a weight ratio of the compound of Formula (Ib-2) to the compound of Formula (Ib-1) in the range of 60:40 to 99:1, in the range of 70:30 to 99:1, in the range of 80:20 to 99:1, or in the range of 90:10 to 99:1. That is, the major component in the mixture is often the compound of Formula (Ib-2).

The compounds of Formula (Ib) can then be treated to replace the hydroxyl group with an enzyme-labile group. Suitable enzyme-labile groups are those described for group $R^2$ in Formula (I).

In some embodiments, the $R^2$ group is a sugar group. Such a group can be introduced into the compounds of Formula (I) by reaction with a brominated compound $R^{2c}$—Br as shown in Reaction Scheme B. The group —$OR^{2c}$ is equal to the group $R^2$ in Formula (I).

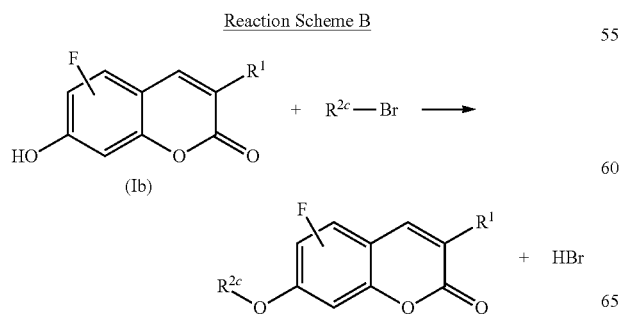

A more specific example is shown in Reaction Scheme B-1 for the addition of the sugar group pyranogalactose. The brominated compound is alpha-bromoacetylpyranogalactose where the hydroxyl groups are protected with acetyl groups. After attachment of the group $R^{2c}$ to the aromatic ring, the acetyl groups are removed by treatment with sodium methoxide. Various brominated and protected sugars are commercially available, for example, from Research Organics in Cleveland, Ohio.

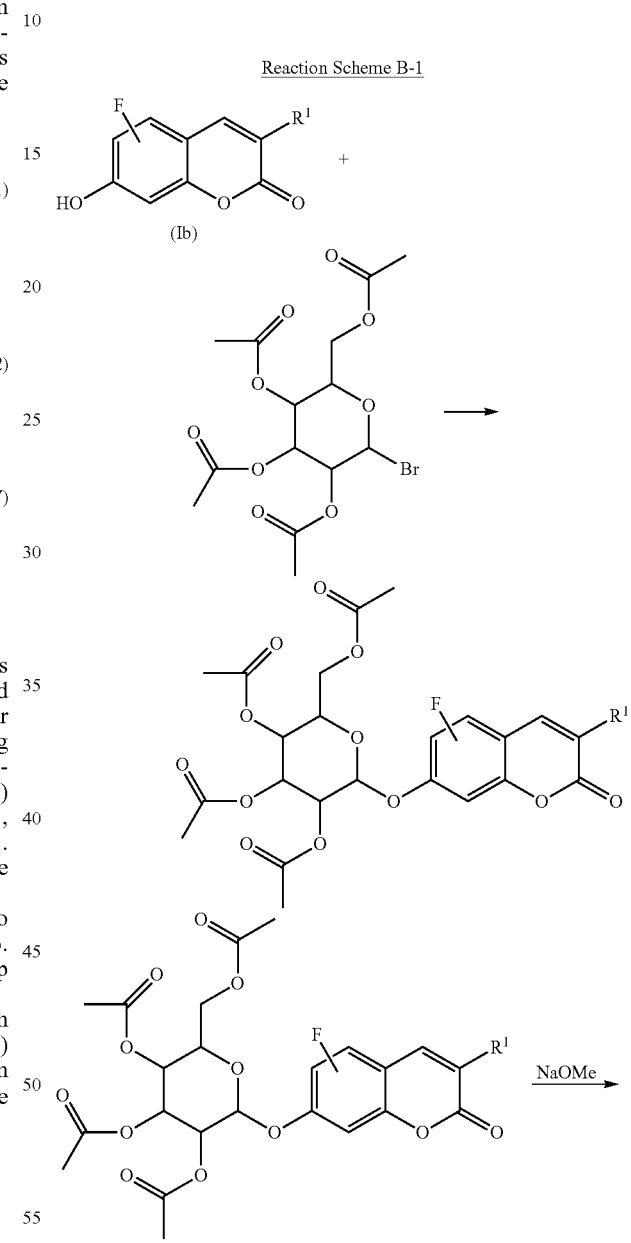

In other embodiments of the compounds of Formula (I), $R^2$ is a phosphate group. The phosphate group can be introduced by reaction of a compound of Formula (Ib) with phosphorous oxytrichloride. In still other embodiments of the compounds of Formula (I), $R^2$ is a sulfate group. The sulfate group can be introduced by reaction of a compound of Formula (Ib) with chlorosulfonic acid. Further details of these reactions are provided, for example, in *Monatshefte fur Chemie,* 116, 65-75 (1985).

Thus, in a second aspect, a method of making a compound of Formula (I) is provided. The method involves the direct fluorination of 2,4-dihydroxybenzaldehyde with a fluorinating agent to form a fluorinated intermediate that is 3-fluoro-2,4-dihydroxybenzaldehyde, 5-fluoro-2,4-dihydroxybenzaldehyde, or a mixture thereof. The fluorinated intermediate is then reacted with a compound of Formula (III)

$$R^1—CH_2—R^{20} \qquad (III)$$

to form the compound of Formula (Ib). In Formula (III), group $R^1$ is —(CO)—$OR^3$, —(CO)—$NR^4R^5$, heterocyclic group, aryl, aralkyl, or cyano and group $R^{20}$ is cyano, a carboxyl group (—COOH), or a group of formula —$COOR^1$.

In a third aspect, a composition is provided. The composition contains a compound of Formula (I) and a water-miscible organic solvent. These compositions can include one or more compounds of Formula (I) and optionally can further include other compounds that are not of Formula (I). The compositions are often solutions.

Suitable water-miscible organic solvents for use in compositions are often those that are capable of dissolving the compounds of Formula (I). Usually, water-miscible organic solvents are selected that can be used to prepare solutions having a concentration of the compound of Formula (I) that is equal to at least 10 millimolar (mM), at least 25 mM, at least 50 mM, at least 100 mM, at least 200 mM, or at least 500 mM. Example water-miscible organic solvents include, but are not limited to, dimethylsulfoxide, dimethylformamide. tetrahydrofuran, N-methyl pyrrolidone, and alcohols (e.g., alcohols having 1 to 6 carbon atoms, 1 to 4 carbon atoms, or 1 to 3 carbon atoms). The solutions can typically be diluted with water or other polar organic solvents such that the compound of Formula (I) remains in solution.

Solutions containing the compound of Formula (I) can optionally include a buffer to adjust or maintain a certain desired pH or pH range. In some embodiments, a pH buffer is in the acidic range. For example, the pH can be in the range of 3 to 10, 4 to 10, 4 to 8, or 4 to 7. Some exemplary buffers include various phosphate buffers, carbonate buffers, acetate buffers, or mixtures thereof.

In many embodiments, the compositions contain a mixture of a compound of Formula (I-1) and a compound of Formula (I-2).

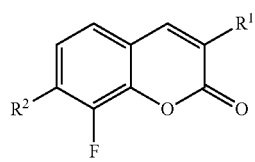

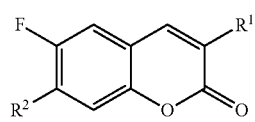

For example, some compositions contain both a compound of Formula (Ib-1) and of Formula (Ib-2).

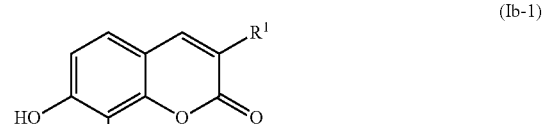

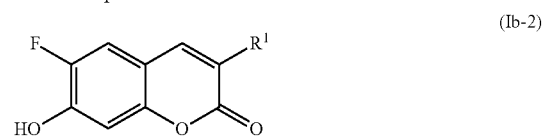

Some of the compositions may further include a non-fluorinated compound of Formula (IV).

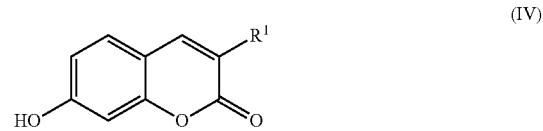

The groups $R^1$ and $R^2$ are the same as defined previously for Formula (I).

Figure 1B:
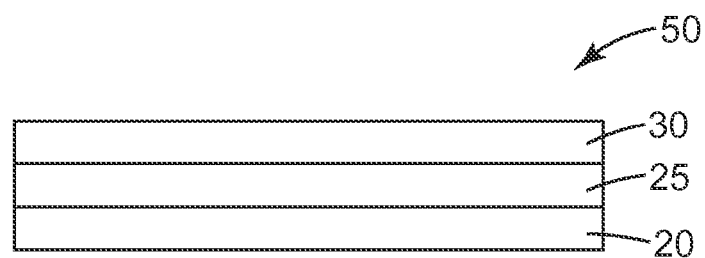

In a fourth aspect, an article is provided. The article includes a first layer that is a support layer and a second layer comprising a compound of Formula (I). The second layer is adjacent to the first layer. As used herein, the term "adjacent" refers to two layers that are in contact with each other or that are separated from each other by one or more intervening layers. Two schematic diagrams of articles are shown in FIG. 1a and FIG. 1b. Article 10 of FIG. 1a contains a support layer 20 and a second layer 30 in contact with the support layer 20. Article 50 of FIG. 1b contains a support layer 20, an adhesive layer 25, and a second layer 30. The adhesive layer is positioned between the support layer and the second layer 30 in FIG. 1b. Such articles can be used to detect the presence or absence of various microorganisms.

Any suitable support layer 20 can be used. The support layer is often selected such that it will not absorb or otherwise be affected by water. Suitable support layers can be, for example, polymeric materials, glasses, ceramic materials, or the like. The support can be transparent or opaque depending on whether or not it is desirable to view various colonies of microorganisms though the support layer. Some support layers include a printed grid pattern (e.g., squares) to facilitate counting colonies of microorganisms. The support layer can be flat or can include various wells. The wells can have any suitable shape and size. In some embodiments, the support layer is a typical Petri dish.

Polymeric materials can be particularly advantageous as the support layer for some applications. The polymeric materials are often in the form of films that are relatively stiff and self-supporting. Example polymeric materials include, but are not limited to, polyesters, polycarbonates, polyolefins (e.g., polyethylene, polypropylene, and copolymers thereof), and polystyrenes. Other suitable substrates include, for example, paper coated with a polyolefin or water resistant coating.

The second layer includes a compound of Formula (I). In many embodiments, the article includes a compound of Formula (Ia) prior to its use to detect the presence or absence of various microorganism.

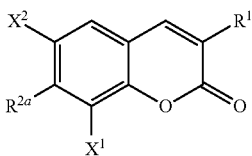

(Ia)

The group $R^{2a}$ refers to an enzyme-labile group. The compounds of Formula (Ia) are fluorogenic compounds that are not fluorescent but that can be converted to a fluorophoric compound that is fluorescent when the enzyme-labile group $R^{2a}$ is hydrolyzed to a hydroxyl group. The resulting fluorophoric compound is of Formula (Ib).

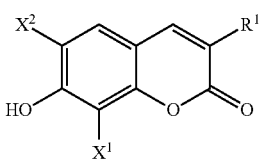

(Ib)

The groups $X^1$, $X^2$, and $R^1$ in Formulas (Ia) and (Ib) are the same as previously defined for compounds of Formula (I).

In some embodiments of the article, the second layer includes a mixture of a compound of Formula (Ia-1) and a compound of Formula (Ia-2) prior to its use to detect the presence or absence of various microorganisms.

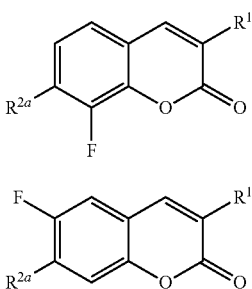

(Ia-1)

(Ia-2)

After reaction with a suitable enzyme, the second layer includes a mixture of a compound of Formula (Ib-1) and a compound of Formula (Ib-2).

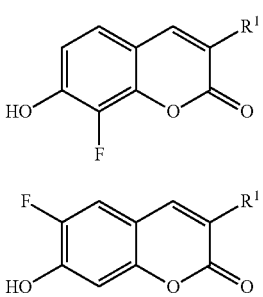

(Ib-1)

(Ib-2)

The second layer can be applied to the first layer using any suitable method. A solution containing the compound of Formula (I) (e.g., a compound of Formula (Ia)) can be applied to the support layer using any suitable method. For example, a solution of the compound of Formula (I) can be applied and then dried to provide a powder (i.e., dehydrated form or dehydrated layer) of the compound of Formula (I) on the surface of the support layer. The second layer can be continuous or discontinuous over the entire surface of the support layer. The second layer can be deposited, for example, in a pattern of wells or regions of the support layer.

In some embodiments, an adhesive layer contacts a surface of the support layer and the compound of Formula (I) is added to an outer surface of the adhesive layer. That is, the article includes an adhesive layer positioned between the support layer and the second layer containing the compound of Formula (I). The compound of Formula (I) can be in the form of a powder or coating that is attached to the support layer using the adhesive layer. The powder or coating can be uniformly deposited or can be deposited in a pattern on the adhesive layer. Suitable adhesives are typically not soluble in water or aqueous medium and are not inhibitory to the growth of microorganisms. Preferably, the adhesive is selected to provide sufficient transparency when wet to view a grid pattern that may be on the surface of the support layer.

If the compound of Formula (I) is present as a powder (e.g., dehydrated form), the thickness of the adhesive layer is typically selected to be less than the diameter of any powder attached to its outer surface. If the adhesive layer is too thin, it may be difficult to sufficiently adhere the powder to the support layer. If the adhesive layer is too thick, however, the powder may be completely embedded within the adhesive layer.

The adhesive layer is often a pressure-sensitive adhesive but other types of adhesives can also be used. In some embodiments, the adhesive can be a silicone-based adhesive such as those described in U.S. Pat. No. 6,703,120 (Ko et al.), which is incorporated herein by reference. In other embodiments, the adhesive layer contains a acrylic copolymer such as, for example, a copolymer of isooctyl acrylate and acrylamide (e.g., in a mole ratio of 90:10 to 98:2 or in a mole ratio of 92:8 to 96:4) or a copolymer of isooctylacrylate and acrylic acid (e.g., in a mole ratio of 90:10 to 98:2, in a mole ratio of 92:8 to 96:4, or in a mole ratio of 94:6 to 96:4). Suitable acrylic copolymer adhesives are further described in U.S. Pat. No. 5,681,712 (Nelson), which is incorporated herein by reference. The adhesive layer can be applied to the support layer using any known process such as knife-coating, extrusion, lamination transfer from a release liner, and the like.

In addition to the compound of Formula (I), the second layer optionally can further include one or more additional components such as a gelling agent, growth medium for growing microorganisms, pH buffer, surfactant, polymeric particles, and the like. These components are often selected to be water soluble such as at or near room temperature. These additional components can be mixed with the compound of Formula (I) as a liquid and then applied directly to the support layer or to the adhesive layer. The liquid can be dried, if desired, after application using any suitable drying method. Alternatively, the compound of Formula (I) can be applied to the support layer or adhesive layer either before or after any additional components that are part of the second layer. In some embodiments, the additional components are mixed with the compound of Formula (I) and then spray dried as a powder onto the surface of the support layer or of the adhesive layer. In other embodiments, the various components are added in a series of liquid compositions and then dried to form the second layer. In some embodiments, regardless of the method of application, the second layer contains little, if any water. That is, the second layer is essentially a dehydrated layer or in a dehydrated form (i.e., the second layer contains only an amount of water associated with equilibration of the second layer with the moisture present in the ambient environment).

In some embodiments, the second layer of the article includes an optional gelling agent. Any suitable gelling agent known in the art can be used. Suitable gelling agents are often soluble in water (e.g., water at or near room temperature) and include, but are not limited to, methyl cellulose, carboxymethyl cellulose, hydroxyethyl cellulose, hydroxypropyl methylcellulose, locust bean gum, guar gum, hydroxypropyl guar, gum arabic (gum acacia), xanthan gum, carageenan, glucomannan, or combinations of these materials. Other suitable gelling agents can be polyacrylamide or super-absorbent materials such as glycol modified polysaccharides and starch-graft-poly(sodium acrylate-co-acrylamides). Some gelling agent can react with water to form a hydrogel.

The second layer optionally can include a surfactant. The surfactant is often added to facilitate dispersion of the selected gelling agent in water. The surfactant can be an anionic surfactant, a cationic surfactant, or a non-ionic surfactant. Examples include, but are not limited to, sodium dodecyl sulfate, sodium dodecylbenzene sulfonate, polyalkyene oxide derivatives, and polysorbates. Examples of polysorbates include, but are not limited to, polyoxyethylene sorbitan monooleate, those commercially available under the trade designation PLURONIC from BASF (Florham Park, N.J.), those commercially available under the trade designation TRITON (e.g., TRITON X-100) from Dow Chemical (Midland, Mich.), those commercially available under the trade designation TWEEN (e.g., TWEEN 20 and TWEEN 80) from Roche (Mannheim, Germany), and the like.

The second layer can include an optional growth medium for growing microorganisms. Any suitable growth medium know in the art can be used. Suitable growth mediums are often in the form of a broth that is soluble in water (e.g., water at or near room temperature). The growth mediums can be selected specifically to optimize the growth of the particular microorganism of interest. Examples include, but are not limited to, fermentable carbohydrates, amino acids, meat extracts, yeast extracts, buffer salts, and the like.

The second layer optionally can include a pH buffer. Any suitable pH buffer can be used. Because the compounds of Formula (I) can advantageously be used under acidic conditions, the pH buffer is frequently selected to be in the acidic range. Suitable pH buffers are often phosphate buffers, acetate buffers, carbonate buffers, or mixtures thereof. The pH is typically at least 4. In some embodiments, the pH is in the range of 3 to 10, 4 to 10, 4 to 8, 4 to 7, or 5 to 8.

Various polymeric particles optionally can be included in the second layer. That is, the second layer of the article can include a compound of Formula (I) and polymeric particles. The polymeric particles can be used to enhance the fluorescence intensity of the compounds of Formula (Ib) after the corresponding compound of Formula (Ia) has reacted with an enzyme present in a sample. The polymeric particles typically sequester the lipophilic fluorogenic and/or fluorophoric compounds from solution. As used herein, the term "sequester" refers to accumulation of a diffusible compound on or within a solid phase (e.g., the polymeric particles). Sequestering tends to limit diffusion of the compounds of Formula (I) and can minimize fluorescence loss due to dilution effects. The polymeric particles can be particularly useful in minimizing diffusion (dilution) of the compounds of Formula (I) when detecting enzymatic activity associated with microorganisms growth in a solid or semi-solid (e.g., hydrogel) media.

Suitable polymeric particles are often prepared from acrylate polymers or copolymers, styrene polymers or copolymers, cellulosic polymers or copolymers, dextran polymers or copolymers, derivatives thereof, or combinations thereof. Suitable polymeric particles include, but are not limited to, those commercially available from Soken Chemical and Engineering in Osaka, Japan under the trade designation MX (e.g., MX-180), MR, MP, SGP, and SX-500, those commercially available from Evonik Industries in Newark, Del. under the trade designation EUDRAGIT (e.g., RLPO and S-1000), those commercially available from Sigma Chemical Co. in St. Louis, Mo. under the trade designation AMBERLITE (e.g., nonionic absorbers and ion exchange resins), those commercially available from Alfa Aesar in Ward Hill, Mass. under the trade designation AMBERLYST (e.g., ion exchange resins), and those commercially available from GE Healthcare in Piscataway, N.J. under that trade designation WHATMAN (e.g., WHATMAN QA 52 and WHATMAN DE 53) and SEPHADEX.

Polymeric particles suitable for sequestering the fluorophoric compounds of Formula (I) typically have a mean particle diameter in the range of 0.01 micrometers to 1 millimeter, in the range of 0.05 micrometers to 20 micrometers, in the range of 0.1 micrometers to 5 micrometers, or in the range of 0.2 micrometers to 2 micrometers.

Any suitable amount of the second layer can be included in the article. When the second layer is in the form of a powder, the second layer often has a coating weight equal to at least 0.4 milligrams per square centimeter ($mg/cm^2$). For example, the coating weight can be at least 0.5 $mg/cm^2$, at least 1 $mg/cm^2$, at least 2 $mg/cm^2$.

Figure 2:
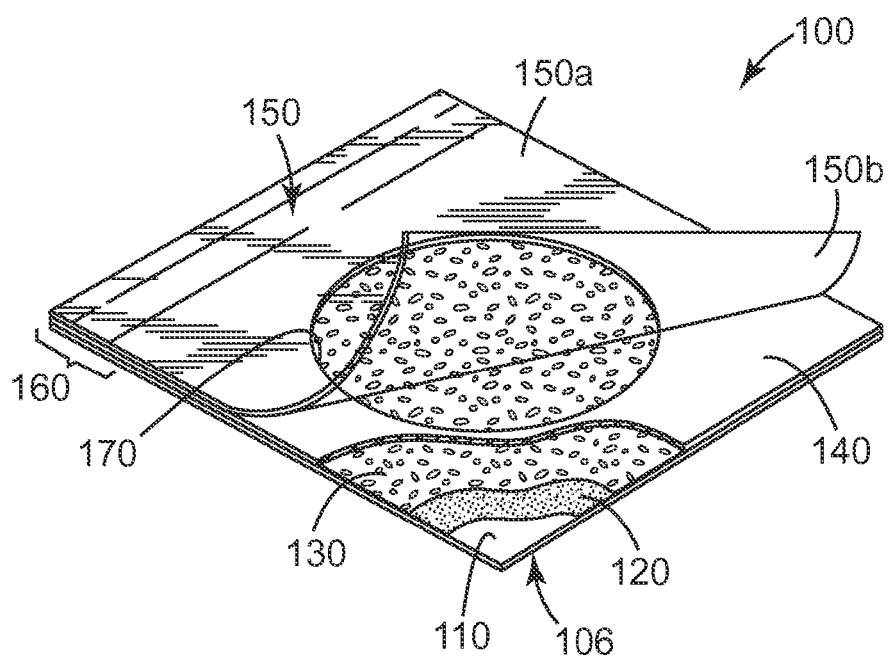
FIG. 2 is an example schematic diagram of a thin film article that can include a compound of Formula (I).

In some embodiments, the article is a thin film culture device such as those described in U.S. Pat. No. 4,565,783 (Hansen et al.), U.S. Pat. No. 5,089,413 (Nelson et al.), and U.S. Pat. No. 5,681,712 (Nelson). The thin film culture devices described in these patents are incorporated here by reference. An example of such an article is shown in FIG. 2. Article 100 includes a support layer 110, an adhesive layer 120, a second layer 130 that includes the compound of Formula (I), a spacer layer 140, and a cover sheet 150. The cover sheet 150 is coupled to the support layer 110 in a hinge area 160.

The support layer 110 is often a relatively stiff film such as, for example, polyester film (e.g., films having a thickness of at least about 100 micrometers), polycarbonate film (e.g., films having a thickness of at least about 100 micrometers), polypropylene or polyethylene film (e.g., films having a thickness of at least about 100 micrometers), polystyrene film (films having a thickness of at least about 300 micrometers), or paper coated with a water-proof coating such as a polyethylene coating. The support layer is coated with the adhesive layer 120. The adhesive layer 120 can be the same as described for the adhesive layer 25 in FIG. 1b. The adhesive layer 120 is positioned between the support layer 110 and the second layer 130. The second layer 130 is the same as described for the second layer 30 in FIGS. 1a and 1b.

The spacer layer 140 in FIG. 2 can be formed from a polymeric material that is hydrophobic (i.e., non-wetting by an aqueous medium), inert to microorganisms, and capable of withstanding sterilization. Suitable materials include, but are not limited to, closed cell polyethylene foam. The spacer layer 140 can include a hole cut through a center region to expose the second layer 130 and to provide a well 170 of predetermined size and shape (e.g., circle, square, oval, or rectangle). The dimensions of the hole determine the area of the second layer 130 that can be exposed to a liquid sample. In some embodiments, the well 170 has a cylindrical shape. The thickness of the spacer 140 and the size of the hole together determine the volume of well 170 and the maximum volume of liquid sample that can be exposed to the second layer 130. The thickness of the spacer 140 is often at least 0.5 millimeters (mm), at least 1 mm, at least 1.5 nm, or at least 2 mm.

Although FIG. 2 shows only a single well 170, a plurality of holes can be cut into the spacer to provide a plurality of wells. For example, the article can include up to 20 or more wells and each well can be used to analyze a different sample for the presence or absence of a target microorganism.

Attached to one edge of the spacer layer 140 is the coversheet 150. The cover sheet has an outer surface 150a and an inner surface 150b. The cover sheet 150 can be attached using any known type of attachment means such as staples, stitches, adhesives, adhesive tapes, and the like. The cover sheet 150 is often selected to be transparent to the human eye, to be impermeable to microorganism, and to be impermeable to water vapor, to be permeable to air, or a combination thereof. Transparency facilitates counting of the microorganism colonies. The cover sheets 150 can function to prevent or minimize undesirable contamination of the second layer 130. Additionally, the cover sheet 150 in combination with the support layer 110 can be used to provide an enclosed environment that will support the growth of microorganism during any incubation period. The cover sheet 150 can be prepared from polyethylene, polypropylene, polyethylene terephthalate, polyvinylidine fluoride, and the like. In some articles, the cover sheet is biaxially oriented polypropylene. The cover sheet 150 can optionally further include an adhesive layer (not shown) and at least one additional layer (not shown) that includes a gelling agent, growth medium, or a combination thereof. Any of these optional layers are typically on the inner surface 150b of the cover sheet that covers the well 170.

The article of FIG. 2 can be used to detect microorganism in a test sample. The test sample can be introduced into the well 170, which exposes the test sample to the second layer 130 in the base of the well 170. When incubated, microorganism in the test sample can grow. If the microorganisms contain an enzyme that can hydrolyze the enzyme-labile group $R^2$ of the compounds of Formula (I) (e.g., groups $R^{2a}$ in the compounds of Formula (Ia)), the resulting fluorophoric compound of Formula (Ib) can be detected using fluorescence spectroscopy. The intensity of the fluorescent signal can be correlated to the concentration of the enzyme and to the concentration of the microorganism.

In a fifth aspect, a method of detecting a microorganism is provided. The method includes providing a fluorogenic compound of Formula (Ia).

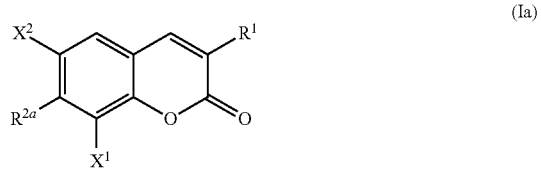

In Formula (Ia), $R^1$ is —(CO)—$OR^3$, —(CO)—$NR^4R^5$, heterocyclic group, aryl, aralkyl, or cyano. Group $R^3$ is alkyl, alkenyl, aryl, or aralkyl. Groups $R^4$ and $R^5$ are each independently hydrogen, alkyl, aryl, or aralkyl. Group $R^{2a}$ is an enzyme-labile group. Either (a) $X^1$ is and $X^2$ is fluoro or (b) $X^1$ is fluoro and $X^2$ is hydrogen. The method further includes incubating a test sample with the compound of Formula (Ia), wherein the test sample contains an enzyme that cleaves group $R^{2a}$ resulting in the formation of a fluorophoric compound of Formula (Ib).

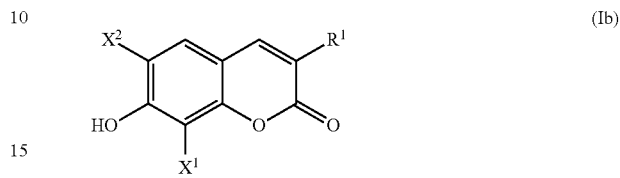

The method still further includes exciting the fluorophoric compound of Formula (Ib) with a first wavelength of light and detecting light emitted at a second wavelength of light that is longer than first wavelength of light. The method can optionally further include sequestering the fluorophoric compound of Formula (Ib) using polymeric particles such as those described above for use in the second layer of the article.

In many embodiments, the compound of Formula (I) is present in an article such as those described including those exemplified in FIGS. 1a, 1b, and 2. The articles often optionally include a gelling agent, growth medium, pH buffer, surfactant, or mixture thereof in the second layer of the article.

Microorganisms that can be detected are those that contain or produce an enzyme that can hydrolyze the enzyme-labile group $R^{2a}$ on the fluorogenic compounds of Formula (Ia). Suitable enzymes include, for example, glycosidase enzymes, esterase enzymes, phosphatase enzymes, sulfatase enzymes, peptidases, lipases, and the like.

Some microorganisms of particular interest that may contain an enzyme that can hydrolyze the enzyme-labile group (i.e., group $R^{2a}$ in Formula (Ia)) include prokaryotic and eukaryotic organisms. Examples include, but are not limited to, Gram positive bacteria, Gram negative bacteria, fungi, protozoa, mycoplasma, yeast, and viruses. Exemplary fungi include both yeasts (including for example, *Saccharomyces cerevisiae, Cryptococcus neoformans, Candida albicans, Candida tropicalis, Candida stellatoidea, Candida glabrata, Candida krusei, Candida parapsilosis, Candida guilliermondii, Candida viswanathii, Candida lusitaniae*, and *Rhodotorula mucilaginosa*) and molds (including for example, *Acremonium, Aspergillus, Cladosporium, Fusarium, Mucor, Penicillium, Rhizopus, Stachybotrys*, and *Trichoderma*) for example. Exemplary bacteria include the following microorganisms: *Acenitobacter Iwoffii, Aeromonas hydrophilia, Aeromonas caviae, Aeromonas sobria, Bacillus cereus, Bacillus stearothermophilus, Bacillus subtilis, Bacillus sphaericus, Bacteroides fragilis, Bacteroides intermedium, Citrobacter freundii, Clostridium perfringens, Enterobacter aerogenes, Enterobacter cloacae, Enterococcus faecium, Enterococcus faecalis, Escherichia coli, Flavobacterium, Haemophilus influenzae, Haemophilus parainfluenzae, Klebsiella pneumoniae, Kocuria varians, Lactococcus lactis, Listeria monocytogenes, Listeria innocua, Mirobacterium esteraromaticum, Mycobacterium fortuitum, Neisseria gonorrhoeae, Organella morganii, Peptostreptococcus anaerobius, Peptococcus magnus, Proteus mirabilis, Pseudomonas* (for example *Pseudomonas aeruginosa, Pseudomonas fluorescens, Pseudomonas pudita*), *Sal-* monella typhimurium, Serratia liquefaciens, Serratia marcescens, Staphylococcus aureus, Staphylococcus epidermidis, Staphylococcus hominis, Staphylococcus simulans, Streptococcus agalactiae B, Streptococcus anginosus, Streptococcus constellatus, Streptococcus faecalis D, Streptococcus mutans, Streptococcus pyogenes, Streptococcus uberis, and Xanthomonas maltophilia.

Suitable test samples can be obtained or derived from a variety of sources. The source can be a solid, liquid, semi-solid, gelatinous material, dispersion, emulsion, suspension, gas (e.g., air), and the like. Example test sample can be clinical samples, environmental samples, food samples, cosmetic samples, beverage samples, water samples, and soil samples. In some embodiments, sample collection devices and sampling techniques can be used to concentrate the test sample or to convert the test sample into a form more suitable for analysis. Some example sample collection devices include, but are not limited to, filters, membranes, adsorption media, sponges, wipes, and swabs.

Various surfaces (e.g., walls, floors, surgical equipment, instruments, food processing equipment) can be tested for the presence of a microorganism by contacting the surface with a sample collection device such as a wipe, sponge, swab, and the like. Example sample collection devices are commercially available under the trade designation 3M QUICK SWAB from 3M Company (St. Paul, Minn.), under the trade designation PURE-WRAPS from Puritan Medical Products Co. LLC (Guilford, Me.), under the trade designation ESWA from Copan Diagnostics, Inc. (Corona, Calif.), and under the trade designation FLOCKEDSWAB from microRheologics, S.r.l. (Brescia, IT).

The wipe, sponge, swab, and the like can then be analyzed directly or transferred to a liquid medium by washing, extraction, and the like with an appropriate solvent or solution. The liquid medium often can include, for example, water, an organic solvent, a buffer, a surfactant, or a combination thereof. The liquid sample can then be analyzed directly or can be subjected to further methods including concentration, precipitation, filtration, centrifugation, dialysis, dilution, inactivation of certain components that might interfere with the analysis, addition of reagents, chemical treatment, and the like.

Other sampling techniques include concentrating the microorganisms using a membrane filter. For example, microporous membrane filters can be used to collect microorganism from a liquid sample or air sample. The average pore diameter of suitable membrane filters are often less than 1 micrometer, less than 0.8 micrometer, less than 0.45 micrometers, or less than 0.2 micrometer. The liquid sample or air sample can be passed through the membrane that has a pore size sufficiently small to retain the microorganisms. Microorganisms can often be retained by, for example, physical entrapment, specific interactions (e.g., antigen-antibody or receptor-ligand interactions), or nonspecific chemical interactions (e.g., hydrophobic adsorption or ion exchange). Some membranes and filters such as those that are relatively thin often can be analyzed directly by placement next to the second layer of the articles described herein. Stated differently, the membranes and filters can be placed in contact with the compound of Formula (I) as well as optional gelling agents, buffers, growth mediums and the like. In some instances, liquid is added to reconstitute (hydrate) the second layer prior to introduction of the filter or membrane.

The test sample, in whatever form, is typically incubated in the presence of the compound of Formula (I). Incubating the test sample with the fluorogenic compound of Formula (Ia) or with the fluorogenic compound plus growth mediums can be accomplished simply by mixing the various components together. The mixture can be agitated and/or heated, if desired. The step of incubating can be undertaken for any amount of time. In embodiments, the test sample and enzyme substrate are allowed to incubate. Any suitable time and temperature can be used for incubation. The incubation can be conducted under aerobic conditions, if desired. For example, the articles in contact with a test sample that may contain microorganisms can be placed in an incubator in the range of 25° C. to 45° C., in the range of 25° C. to 40° C., or in the range of 30° C. to 40° C. for 12 hours, 18 hours, 24 hours, 36 hours, 48 hours, 72 hours, 96 hours, or even longer than 96 hours.

The incubated sample can be irradiated with light having a first wavelength for an amount of time that is sufficient for the fluorophoric compound of Formula (Ib) to emit light of a second wavelength that is longer than the first wavelength. Both the first and second wavelengths of light typically are in the ultraviolet, visible, or infrared region of the electromagnetic spectrum. The incubated sample is often irradiated with the first wavelength of light for fractions of a second to tens of seconds.

The compounds of Formula (I) can be advantageously used to detect the presence or absence of a microorganism in a test sample having a pH in the acidic region. While not wishing to be bound by theory, the presence of the fluoride group on the compound of Formula (I) extends the useful pH range in which the compounds can be useful. That is, surprisingly the compounds of Formula (Ib) are fluorophores over an extended pH range including into the acidic range. Compared to many other non-fluorinated coumarin-based fluorescent indicators, the fluorescent intensity tends to remain relatively constant over time in an acidic environment.

In some embodiments, the compounds of Formula (Ib) can be excited with a wavelength of light near 400 nanometers or longer. For example, the compounds can be excited at a wavelength near 410 nm, 420 nm, 430 nm, 440 nm, or 450 nm. This can be advantageous for some sample such as those containing biological materials. Samples containing biological materials often have a significant background signal when excited at about 365 nanometers but not when excited at about 400 nanometers or longer. Excitation at these wavelengths can allow the use of various low cost laser diode light sources such as InGaN.

Compounds of Formula (Ib) that are particularly useful when excited at a wavelength of about 400 nanometers or longer are those with a $R^1$ group that is a heterocyclic compound. More particularly, suitable $R^1$ groups often have a five member heterocyclic ring with two double bonds in the ring. Such heterocyclic rings can have either one or two heteroatoms. Example heterocyclic groups include, but are not limited to, thienyl, pyrrolyl, furanyl, imidazolyl, oxazolyl, thiazolyl, isoxazolyl, and isothiazolyl. Other example heterocyclic groups include, but are not limited to, indolyl, isoindolyl, benzofuranyl, benzothienyl, benzimidazolyl, N-substituted benzimidazolyl, benzthiazolyl, benzoxazolyl, and benzisoxazolyl.

The light emitted by the excited fluorophoric compound of Formula (Ib) can be detected using any known detector. Detectors, such as photomultiplier tubes, avalanche photo-diodes, charge coupled devices (CCDs), photodiodes, and other active devices may be utilized. The detector can also be combined with various commonly utilized filters and optical components.

Once the emitted light has been detected, various additional steps can optionally be carried out. One optional step is that the emitted light can be quantified in order to estimate the amount of microorganisms in the test sample. This can be accomplished by comparing the integrated intensity of emitted light from the test sample with the integrated intensity of emitted light (under the same conditions) from one or more than one standard samples. A relative comparison can also be carried out by, for example, comparing the fluorescent intensity at two different times (for example before and after a sterilization procedure).

Another additional step that can optionally be carried out is to form an image of the detected light. In an embodiment, a CCD (or other detector) that has a number of individually addressable photosensitive detector elements can enable the collection of fluorescent data from the sensor or sensor array on a pixel by pixel basis. This array can be used in combination with an illumination source and proper collection optics to obtain an image of, for example sites of growing microbial colonies on an inoculated two dimensional surface (for example, using an article similar to that shown in FIG. 2 but with multiple wells). The resulting electronic image can be transmitted to the processor assembly, where image analysis software can be used to enhance the contrast of the image and to count the number of fluorescent zones automatically (or a user can count the number of zones manually).

Suitable measurement devices include those commercially available from 3M Company in Saint Paul, Minn. under the trade designation 3M ATTEST BIOLOGICAL MONITORING SYSTEM. With this measurement device, the incubated sample can be irradiated for about a second with a first wavelength of light. This irradiation time is typically sufficient to obtain a stable excited state and integrate the intensity of emissions. In embodiments that can be utilized use an article such as shown in FIG. 2, the incubated article can be irradiated for up to tens of seconds.

Kits are also disclosed herein. Kits as disclosed herein can include a fluorogenic compound of formula I, and other components. Kits can also include containers configured to mix at least the fluorogenic compound and the sample to be tested. In embodiments, the optional container can come preloaded with the fluorogenic compound; or in embodiments, the optional container can come preloaded with a growth media containing the fluorogenic compound. An example of a container that can be preloaded with a growth media containing a fluorogenic compound is the article shown in FIG. 2. For example, the fluorogenic compound of Formula (Ia) can be used in an article such as a 3M PETRIFILM, a trade designation of 3M in Saint Paul, Minn.

Multiple items are provided such as compounds, compositions, articles, methods of detecting a microorganism, and methods of synthesizing compounds.

A first item is compound of Formula (I).

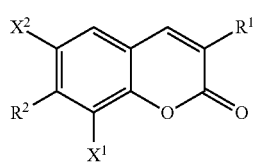

In Formula (I), the group $R^1$ is —(CO)—$OR^3$, —(CO)—$NR^4R^5$, heterocyclic group, aryl, aralkyl, or cyano. The group $R^2$ is hydroxyl or an enzyme-labile group. The group $R^3$ is alkyl, alkenyl, aryl, or aralkyl. Groups $R^4$ and $R^5$ are each independently hydrogen, alkyl, aryl, or aralkyl. Either (a) $X^1$ is hydrogen and $X^2$ is fluoro or (b) $X^1$ is fluoro and $X^2$ is hydrogen.

A second item is the compound of item 1, wherein $R^2$ is a sugar group, sugar acid group, amino sugar group, carboxyl-terminated amino acid group, carboxyl-terminated peptide group, ester group, ester-containing group, phosphate group, or sulfate group.

A third item is the compound of item 1 or 2, wherein $R^2$ is a sugar group that is a monosaccharide group or disaccharide group.

A fourth item is the compound of any one of items 1 to 3, wherein $R^1$ is —(CO)—$OR^3$ where $R^3$ is an alkyl.

A fifth item is the compound of any one of items 1 to 4, wherein $R^1$ is a heterocyclic group having a five-member heterocyclic ring.

A sixth item is the compound of any one of items 1 to 5, wherein $R^1$ is a heterocyclic group having a five-member heterocyclic ring fused to a benzene ring.

A seventh item is a composition comprising a water-miscible organic solvent and a compound of Formula (I).

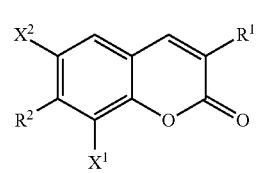

In Formula (I), the group $R^1$ is —(CO)—$OR^3$, —(CO)—$NR^4R^5$, heterocyclic group, aryl, aralkyl, or cyano. The group $R^2$ is hydroxyl or an enzyme-labile group. The group $R^3$ is alkyl, alkenyl, aryl, or aralkyl. Groups $R^4$ and $R^5$ are each independently hydrogen, alkyl, aryl, or aralkyl. Either (a) $X^1$ is hydrogen and $X^2$ is fluoro or (b) $X^1$ is fluoro and $X^2$ is hydrogen.

An eighth item is the composition of item 7, wherein the composition comprises a mixture of a compound of Formula (I-1) and a compound of Formula (I-2).

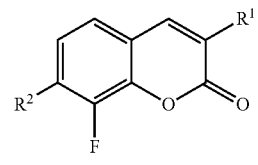

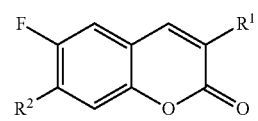

A ninth item is an article comprising a) a first layer that is a support layer and b) a second layer adjacent to the support layer, wherein the second layer comprises a compound of Formula (I).

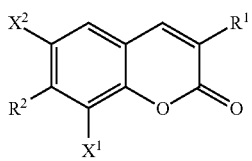

(I)

In Formula (I), the group $R^1$ is —(CO)—$OR^3$, —(CO)—$NR^4R^5$, heterocyclic group, aryl, aralkyl, or cyano. The group $R^2$ is hydroxyl or an enzyme-labile group. The group $R^3$ is alkyl, alkenyl, aryl, or aralkyl. Groups $R^4$ and $R^5$ are each independently hydrogen, alkyl, aryl, or aralkyl. Either (a) $X^1$ is hydrogen and $X^2$ is fluoro or (b) $X^1$ is fluoro and $X^2$ is hydrogen.

A tenth item is the article of item 9, wherein the second layer comprises a mixture of a compound of Formula (I-1) and a compound of Formula (I-2).

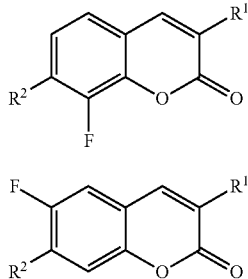

(I-1)

(I-2)

An eleventh item is the article of item 9 or 10, wherein the second layer further comprises a gelling agent, growth medium, or a combination thereof.

A twelfth item is the article of any one of items 9 to 11, wherein the second layer is dehydrated.

A thirteenth item is the article of any one of items 9 to 12, wherein the second layer further comprises polymeric particles.

A fourteenth item is the article of item 13, wherein the polymeric particles comprise an acrylate polymer or copolymer, styrene polymer or copolymer, cellulosic polymer or copolymer, dextran polymer or copolymer, derivatives thereof, or combinations thereof.

A fifteenth item is the article of item 13 or 14, wherein the polymeric particles have an average particle diameter in a range of 0.01 micrometers to 1 micrometer.

A sixteenth item is a method of detecting a microorganism, the method includes providing a fluorogenic compound of Formula (Ia).

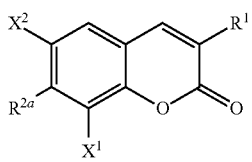

(Ia)

In Formula (Ia), group $R^1$ is —(CO)—$OR^3$, —(CO)—$NR^4R^5$, heterocyclic group, aryl, aralkyl, or cyano. Group $R^{2a}$ is an enzyme-labile group. Group $R^3$ is alkyl, alkenyl, aryl, or aralkyl. Groups $R^4$ and $R^5$ are each independently hydrogen, alkyl, aryl, or aralkyl. Either (a) $X^1$ is hydrogen and $X^2$ is fluoro or (b) $X^1$ is fluoro and $X^2$ is hydrogen. The method further includes incubating a test sample with the fluorogenic compound of Formula (Ia), wherein the test sample contains an enzyme from the microorganism and the enzyme cleaves (i.e., hydrolyzes) the group $R^{2a}$ resulting in the formation of a fluorophoric compound of Formula (Ib).

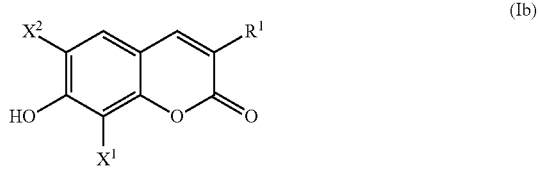

(Ib)

The method still further includes exciting the fluorophoric compound of Formula (Ib) with a first wavelength ranged of light and detecting light emitted at a second wavelength of light that is longer than first wavelength of light.

A seventeenth item is the method of item 16, wherein the first wavelength of light and the second wavelength of light are in the ultraviolet, visible, or infrared region.

An eighteenth item is the method of item 16 or 17, wherein the step of incubating the test sample with the fluorogenic compound comprises adding the test sample in a liquid form to a dehydrated layer containing the fluorogenic compound of Formula (Ia) and a growth medium.

A nineteenth item is the method of any one of items 16 to 18, wherein the method further comprises sequestering the compound of Formula (Ib) on polymeric particles.

A twentieth item is the method of item 19, wherein the polymeric particles have an average particle diameter in a range of 0.01 micrometers to 1 micrometer.

A twenty-first item is a method of preparing a compound of Formula (Ib).

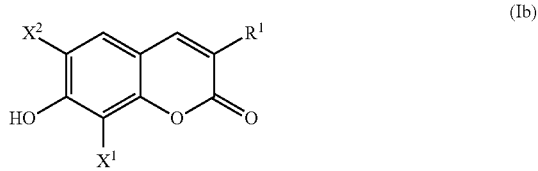

(Ib)

In Formula (Ib), group $R^1$ is —(CO)—$OR^3$, —(CO)—$NR^4R^5$, heterocyclic group, aryl, aralkyl, or cyano. Group $R^3$ is alkyl, alkenyl, aryl, or aralkyl. Groups $R^4$ and $R^5$ are each independently hydrogen, alkyl, aryl, or aralkyl. Either (a) $X^1$ is hydrogen and $X^2$ is fluoro or (b) $X^1$ is fluoro and $X^2$ is hydrogen. The method involves the direct fluorination of 2,4-dihydroxybenzaldehyde with a fluorinating agent to form a fluorinated intermediate that is 3-fluoro-2,4-dihydroxybenzaldehyde, 5-fluoro-2,4-dihydroxybenzaldehyde, or a mixture thereof. The fluorinated intermediate is then reacted with a compound of Formula (III)

$R^1$—$CH_2$—$R^{20}$ (III)

to form the compound of Formula (Ib). In Formula (III), group $R^1$ is the same as defined for Formula (Ib) and group $R^{20}$ is cyano, a carboxyl group (—COOH), or a group of formula —$COOR^1$.

EXAMPLES

All parts, percentages, ratios, and the like used in the following examples are by weight, unless noted otherwise.

SELECTFLUOR is a trade designation of Air Products of Allentown, Pa. for a fluorinating reagent that includes (1-chloromethyl-4-fluoro-1,4-diazoniabicyclo[2.2.2]octane bis(tetrafluoroborate)), diethylmalonate, and sodium methoxide.

Acetonitrile, acetic acid, silica gel, ethyl acetate, hexane, triethylamine, acetic anhydride, concentrated HCl, magnesium sulfate, DMSO (dimethyl sulfoxide), dextrose, silica gel, yeast extract and pancreatic digest of casein were obtained from EMD (Gibbstown, N.J.).

2,4-dihydroxybenzaldehyde was obtained from Eastman Chemical Company (Kingsport, Tenn.).

Morpholine was obtained from Matheson, Coleman and Bell (Norwood, Ohio).

2-thiopheneacetic acid, sodium pyruvate, dibasic potassium phosphate and monobasic potassium phosphate were obtained from Sigma-Aldrich (Milwaukee, Wis.).

Anhydrous methanol was obtained from J. T. Baker (Phillipsburg, N.Y.).

Alpha-bromoacetylpyranogalactose was obtained from Research Organics (Cleveland, Ohio).

Sodium hydroxide (1 N) was obtained from VWR (West Chester, Pa.).

MX-180 is a trade designation for monodisperse acrylate particles that were obtained from Soken Chemical and Engineering (Osaka Japan).

Locust bean gum was obtained from CP Kelco (Atlanta, Ga.).

Xanthan gum was obtained from CP Kelco (Atlanta, Ga.).

The release liner is available from Loparex LLC (Hammond, Wis.).

The compound 3-carboxyethyl-7-hydroxycoumarin was prepared according to Chilvers et. al., *J. Appl. Microbio.*, 91, 1118-1130 (2001).

The compounds 3-thienylumbelliferone and 3-thienylumbelliferone-pyanogalactoside (TU-gal) were prepared as described in U.S. Pat. No. 6,566,508 (Bentsen et al.). The preparation procedures are incorporated herein by reference.

The compound 2-cyanomethylbenzimidazole was prepared according to Copeland and Day, *Journal of the American Chemical Society*, 1943, 65, 1072 (1943).

The compound 3-benzimidazolyl-7-hydroxycoumarin (BiU) was prepared according to Elnagdi et. al., *Journal of Chemical Research (M)*, 375 (1997).

Example 1

Preparation of fluorinated 2,4-dihydroxybenzaldehyde

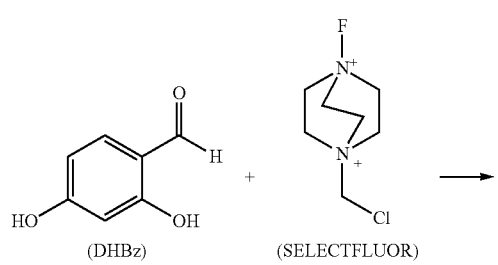
(DHBz)   (SELECTFLUOR)

-continued

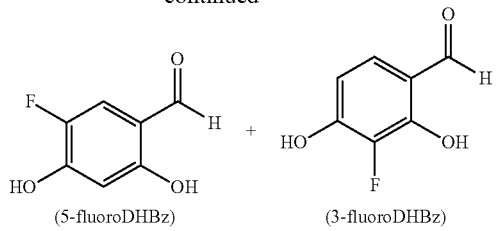
(5-fluoroDHBz)   (3-fluoroDHBz)

A solution was prepared by dissolving 12.230 grams (34.5 millimoles) of a fluorinating reagent (SELECTFLUOR reagent) in 400 milliliters (mL) of acetonitrile from a freshly opened bottle (0.0027 weight percent $H_2O$) in a round bottom flask. After the fluorinating reagent dissolved completely, 7.00 grams (50.6 millimoles) of 2,4-dihydroxybenzaldehyde (DHBz) was added and the flask was closed with stopper having a nitrogen inlet, and the contents were stirred with a magnetic stirring bar at room temperature (about 22° C.). After two days, NMR spectra indicated a conversion of about 29 mole percent of the DHBz and 95 mole percent consumption of the SELECTFLUOR reagent. The solution was bubbled with nitrogen for about 30 minutes and then another 12.29 grams (34.7 millimoles) of SELECTFLUOR reagent was added. The solution was stirred continuously in a freezer for 2 days and then at room temperature for 3 days.

After seven days, the cloudy suspension was filtered to yield a yellow solution and a white precipitate. The precipitate was dried on the filter and the filtrate was dried in vacuo. The dried residue from the filtrate was stirred with 200 mL of diethyl ether for about an hour and then filtered, yielding a yellow solid and a yellow filtrate. The dried white and yellow solids weighed 6.05 grams and 15.72 grams, respectively. NMR on each solid (DMSO-d6) was consistent with a SELECTFLUOR product, with no indication of benzaldehyde derivatives. The total amount of solids was 21.77 grams. Complete recovery of the SELECTFLUOR reagent (assuming the active F is replaced by H) should produced about 23.3 grams.

The yellow diethyl ether solution was dried under vacuum conditions. NMR results indicated a mixture of DHBz, 5-fluoro-DHBz (5-F), and 3-fluoro-DHBz (3-F) in a ratio of 0.41:0.48:0.11 with minor amounts of impurities. The mass of yellow solid was 7.52 grams. The theoretical yield based on these ratios was 7.53 grams, indicating complete recovery of benzaldehyde products. The yellow solid was recrystallized by dissolving in hot water and cooling slowly at ambient temperature, then filtered and dried.

Example 2

Preparation of partially fluorinated 3-ethylcarboxylate-7-hydroxycoumarin (FEHC)

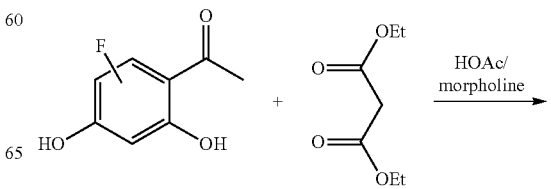

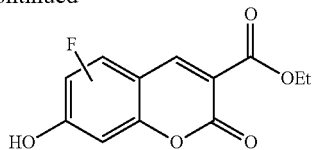

A solution was prepared by adding 2.804 grams of an ether-soluble mixture (approximately 19 millimoles) of fluorinated dihydroxybenzaldehyde from Example 1 to 15 mL of methanol from a freshly opened bottle (0.002 wt % water) in a round bottom flask fitted with a nitrogen inlet, and stirred under nitrogen. A 3.3 mL (22 millimoles) volume of diethylmalonate was added and the solution was heated to reflux for 30 minutes. A solidified mixture of 200 microliters (μL) of morpholine and 50 μL of acetic acid was added, and the reaction solution immediately turned brown. The solution was heated for 2 hours, after which the solution was cooled briefly at ambient temperature for about 30 minutes and then refrigerated overnight.

A small amount of white-yellow needle-like crystals formed that were filtered, and dried on the filter. $^1$H and $^{19}$F NMR spectra (DMSO-d6) were consistent with a mixture of 3-ethylcarboxylate-7-hydroxycoumarin (EHC), 6-fluoro-EHC (6-FEHC) and 8-fluoro-EHC (8-FEHC)

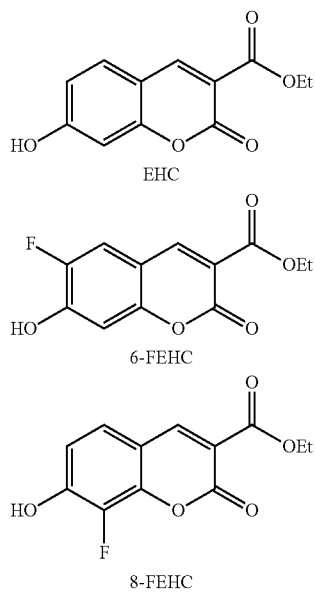

having a ratio of 1:0.7:0.3, the structures of which are shown above.

The mixture was heated again to reflux for 3 hours and then allowed to cool overnight, leading to crystallization. The crystals were washed out of the flask with diethyl ether, which led to considerable further precipitation.

Partially fluorinated EHC (a mixture of EHC, 6-FEHC, and 8-FEHC in a ratio of 1:0.7:0.3), which is referred to as FEHC, was dissolved in DMSO at a concentration of 1 milligram per milliliter (mg/mL). A 96 well plate was prepared with each well containing 100 microliters of 100 mM phosphate buffer at pH values ranging from 8.0 to 2.5 in 0.5 unit increments. A 10 microliter volume of the FEHC solution was added to each well. A set of 10× diluted wells were also prepared to eliminate artifacts due to self-quenching of the fluorophore at high concentrations. The 10× dilutions were prepared by diluting the 1 mg/mL solution to 0.1 mg/mL in DMSO, and then adding 10 microliters of this solution to 100 microliters of 100 mM phosphate buffer in each of the wells.

The absorption spectra from 250 nanometers (nm) to 500 nm were recorded using a SPECTRAMAX M5 fluorescence plate reader (available from Molecular Devices of Sunnyvale Calif.) for each pH value.

Figure 3:
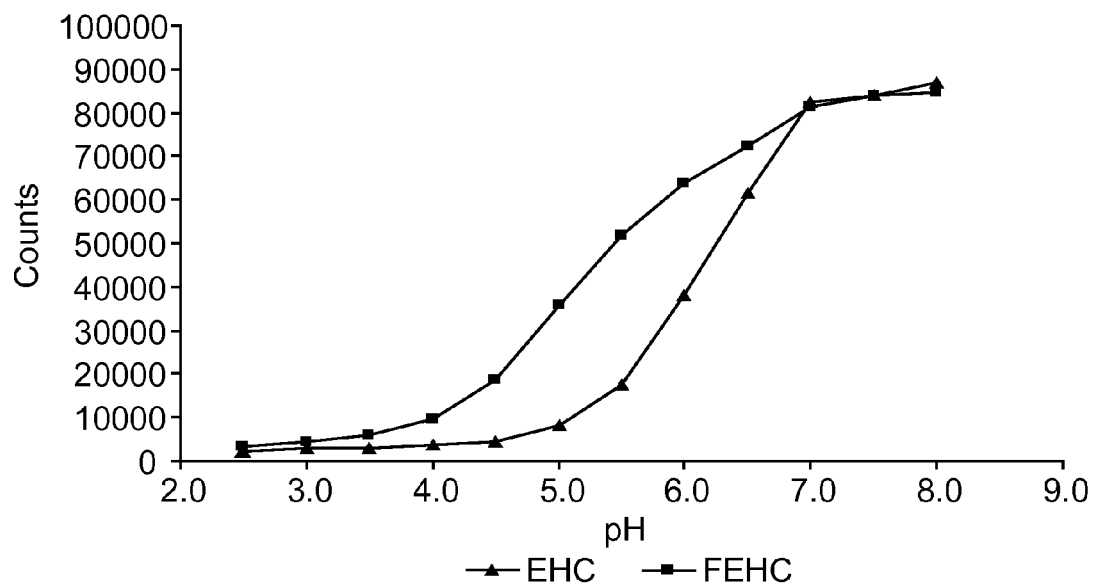
FIG. 3 shows emission at 450 nanometers (nm) (with excitation at 400 nm) for a mixture, which is referred to as FEHC, containing 6-fluoro-3-ethylcarboxylate-7-hydroxy-coumarin (6-FEHC) and 8-fluoro-3-ethylcarboxylate-7-hydroxycoumarin (8-FEHC) as a function of pH compared to 3-ethylcarboxylate-7-hydroxycoumarin (EHC).

Emission spectra at wavelengths from 410 nm to 700 nm were also recorded on the SPECTRAMAX M5 fluorescence plate reader at an excitation wavelength of 400 nm over the range of pH values in the plate. The maximum emission occurred at a wavelength of 450 nm. FIG. 3 shows a graph of fluorescence counts at 450 nm (with excitation at 400 nm) versus pH for EHC and FEHC. Absorbance and emission maxima for FEHC as a function of pH were the same as those for standard EHC. However at pH values between 4.5 and 6.5 the absorbance at 400 nm (and emission at 450 nm) was higher for FEHC than EHC. FEHC showed enhanced fluorescence at pH values from slightly below 7 down to about 2.5.

Example 3

Separation of FEHC by Chromatography

Partially-fluorinated EHC (1.5 grams of FEHC) from Example 1 was separated in a chromatography column over silica gel with a 60/40 mixture of ethyl acetate and hexane. A total of twenty 30 mL fractions were collected, checked by thin layer chromatography, and combined where possible. Fraction 6 of the eluent began precipitating shortly after collection, and eventually fractions 4 to 8 showed signs of precipitation. The column was washed with two more volumes of about 200 mL of an 80/20 mixture of ethyl acetate/hexane followed by 200 mL of ethyl acetate. The solvent was removed from each of these last two fractions with a rotavap. A mixture having a 95:5 weight ratio of 6-FEHC and 8-FEHC was isolated.

A 96 well plate was prepared according to the procedure described in Example 2 except that a 10 microliter volume of a solution of 1 mg/mL of the 95:5 mixture dissolved in DMSO was added to each well with the phosphate buffer.

Figure 4:
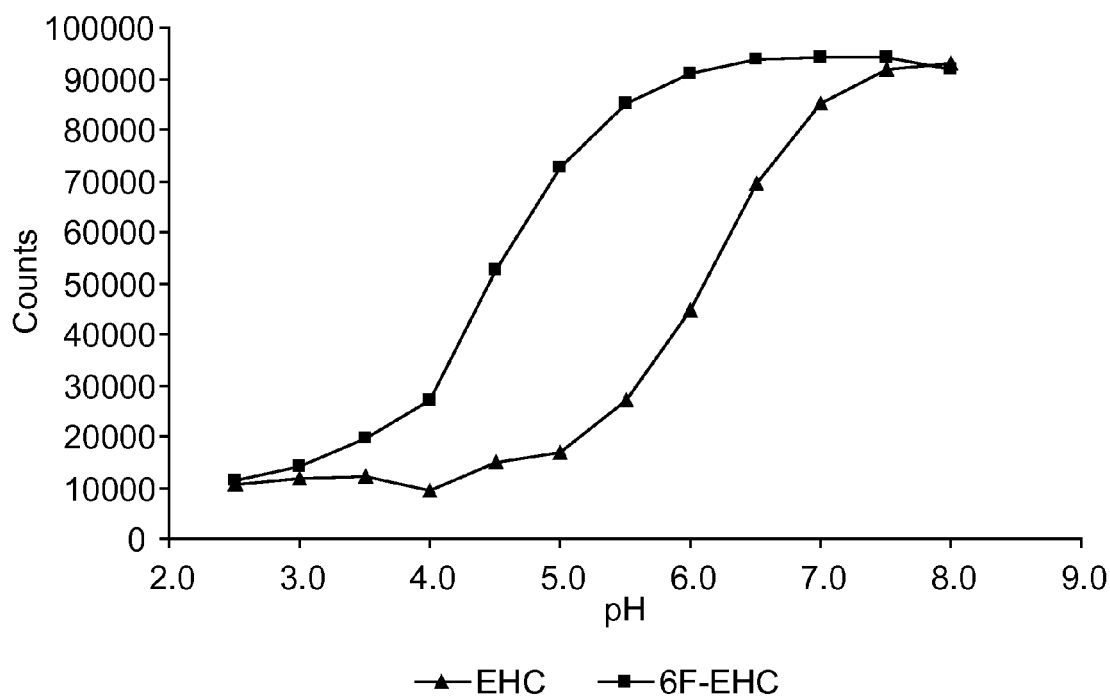
FIG. 4 shows emission at 445 nanometers (with excitation at 400 nm) for 6-FEHC as a function of pH compared to EHC.

The absorption at 400 nm and emission at 450 nm over the range of pH values were recorded on a SPECTRAMAX M5 fluorescence plate reader. The spectra for a mixture of 6-FEHC and 8-FEHC having a 95:5 weight ratio, which is referred to as 6-FEHC, were compared to spectra for EHC alone in FIG. 4. FIG. 4 shows a drop in pKa from about 6.5 to about 4.5 by the addition of fluorine. This was the pH at about the midpoint of the plot of fluorescence counts.

Example 4

Preparation and spectroscopy of partially fluorinated 3-benzimidazolylumbelliferone (FBiU)

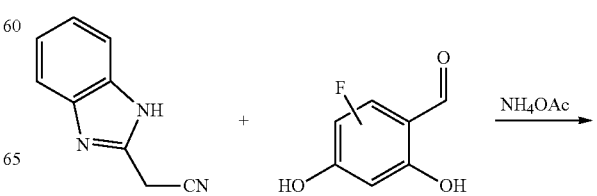

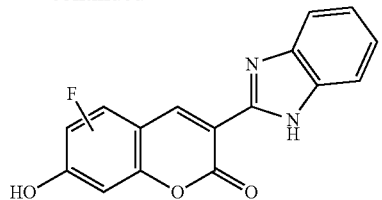

A solution was prepared by mixing 0.215 grams of 2-cyanomethylbenzimidazole (1.4 millimoles) with 0.213 grams fluorinated dihydroxybenzaldehyde from Example 1 (1.4 millimoles), 0.226 grams ammonium acetate (2.9 millimoles), and ethanol (2 mL). The solution was heated to reflux for 1.5 hours. It was then allowed to cool, stirred for a further hour, then filtered, washed on the filter with approximately 20 mL ethanol and dried at room temperature overnight in a vacuum oven. The yield of the dried orange solid was 332 milligrams.

The resulting partially fluorinated 3-benzimidazolylumbelliferone (referred to as FBiU), was dissolved in DMSO at a concentration of 1 milligram per milliliter (mg/mL). A 96 well plate was prepared with each well containing 100 microliters of 100 mM phosphate buffer at pH values ranging from 8.0 to 2.5 in 0.5 unit increments. A 10 microliter volume of the FBiU solution was added to each well. A set of 10× diluted wells were also prepared to eliminate artifacts due to self-quenching of the fluorophore at high concentrations. The 10× dilutions were prepared by diluting the 1 mg/mL solution to 0.1 mg/mL in DMSO, and then adding 10 microliters of this solution to 100 microliters of 100 mM phosphate buffer in each of the wells.

The absorption spectra from 300 nanometers (nm) to 700 nm were recorded for the 10× diluted wells using a SPECTRAMAX M5 fluorescence plate reader (available from Molecular Devices of Sunnyvale Calif.) for each pH value.

Emission spectra at wavelengths from 470 nm to 655 nm were also recorded on the SPECTRAMAX M5 fluorescence plate reader at an excitation wavelength of 450 nm over the range of pH values in the plate. The maximum emission occurred at a wavelength of 495 nm. Absorption and emission spectra were recorded similarly for unfluorinated 3-benzimidazolylumbelliferone (BiU).

Figure 5:
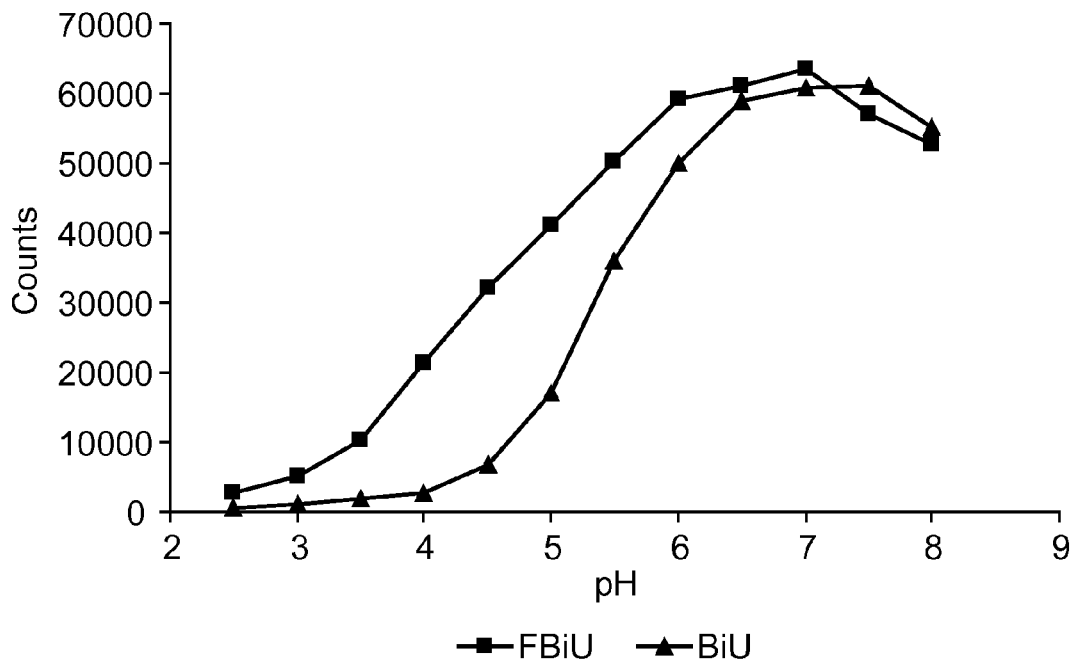
FIG. 5 shows emission at emission at 495 nm (with excitation at 450 nm) for 3-benzimidazolylumbelliferone (BiU) and fluorinated 3-benzimidazolylumbelliferone as a function of pH.

FIG. 5 shows a graph of fluorescence counts at 495 nm (with excitation at 450 nm) versus pH for FBiU compared to BiU. Absorbance and emission maxima for FBiU as a function of pH were the same as those for standard BiU over this pH range. However, FBiU showed enhanced fluorescence at pH values from above 6 down to about 2.5.

Example 5

Preparation of fluorinated 3-thienylumbelliferone (FTU)

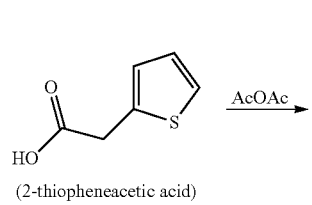
(F-DHBz) (2-thiopheneacetic acid)

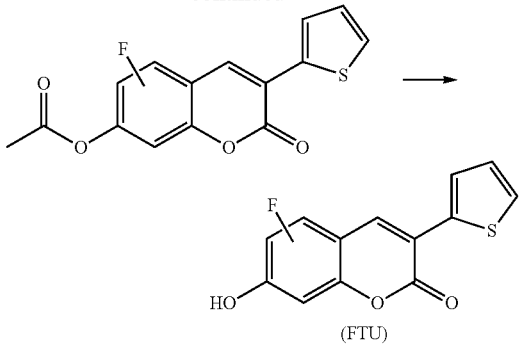
(FTU)

A solution was prepared by stirring 2.006 grams (13.5 millimoles) of fluorinated dihydroxybenzaldehyde from Example 1 with 1.93 grams (13.5 millimoles) of 2-thiopheneacetic acid in a round bottom flask with a magnetic stirring bar. Then 2.4 mL of triethylamine was added, followed by 12 mL of acetic anhydride. The flask was sealed with a stopper equipped with a nitrogen inlet, and heated in an oil bath at about 120° C. for about 2 hours under nitrogen. Analysis by thin layer chromatography (TLC, 60:40 ethyl acetate and hexane) showed two bright blue fluorescent spots fairly close together and little indication of the residual starting material. The solution was allowed to cool to about room temperature. A brown solid was formed that was added to about 100 mL of DI water and stirred for about an hour and then filtered, yielding a yellow filtrate with a little fluorescence and an ochre solid. The $^{19}$F NMR of the solid showed two peaks with the splitting in a 5:1 ratio at −132.9 ppm (dd; 9.9, 6.6 Hz) and −149.9 ppm (d, 6.6 Hz) which was consistent with the expected structure of the reaction product.

The solid material was dried overnight at room temperature in a vacuum oven and the yield was 3.54 grams. The theoretical yield is 3.87 grams (over 91% yield). A small sample was set aside, and the remainder was stirred in 50 mL methanol. A mixture of about 30 mL of HCl in 30 mL of deionized (DI) water was added and the suspension was heated to reflux about 2 hours; the suspension turned green after about the first 30 minutes of refluxing. The suspension was allowed to cool while stirring for 1.5 hours, and then 200 mL of DI water was added and for about 15 minutes. The suspension was filtered to yield a dark green solid and a pale yellow filtrate. The solid was dried on the filter in a vacuum oven overnight at room temperature.

$^1$H NMR spectra on a sample taken before vacuum drying showed sharp and distinct phenol peaks, with the expected integration (relative to the vinyl) at 10.6-11.2 ppm. The aromatic region was complex, but the overall integrals were consistent with the expected desired product mix. $^{19}$F NMR had two peaks in a 5:1 ratio at −139.5 ppm (dd, 10.5, 7.6 Hz) and −160.3 ppm (d, 7.5 Hz) corresponding to fluorinated thienylumbelliferones (FTU), which was a mixture of 6-fluoro-FTU (6-FTU) and 8-fluoro-FTU (8-FTU). Yield from de-acetylation was 2.82 grams (93% yield).

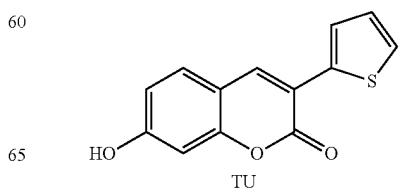
TU

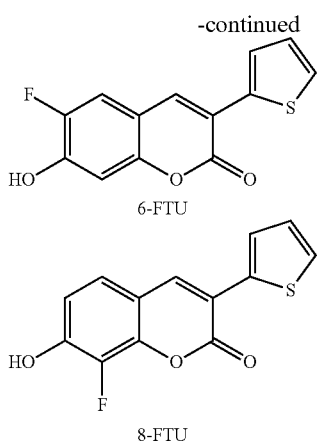

6-FTU

8-FTU

Example 6

Preparation of acetylated FTU-pyranogalactoside (FTU-gal)

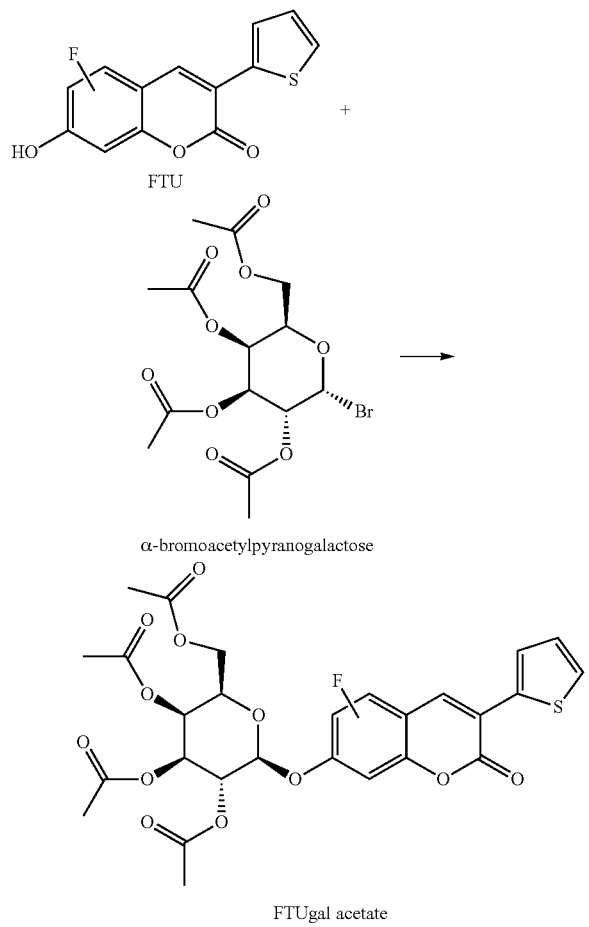

α-bromoacetylpyranogalactose

FTUgal acetate

A slight excess of the fluorinated coumarin mixture from Example 5 (1.52 grams, 6 millimoles) was stirred with 2.06 grams (5 millimoles) of α-bromoacetylpyranogalactose, 10 mL of 1N NaOH, and 20 mL of acetone within a round bottom flask with a magnetic stirring bar at room temperature for five days. After removing the acetone under vacuum, the residue was extracted with about 100 mL of chloroform. A 1N NaOH solution was used to extract the residual unreacted products, and the residue in chloroform was washed with three 100 mL volumes of DI water. The organic phase was dried over MgSO$_4$, filtered, and then the solvent removed under vacuum to yield acetylated FTU-pyranogalactoside (FTU-gal acetate). $^1$H and $^{19}$F NMR analyses were both consistent with a mixture of 6-FTU-gal acetate, 8-FTU-gal acetate, and non-fluorinated product in a weight ratio of 0.53:0.11:0.37.

Example 7

Deprotection of acetylated FTU-pyranogalactoside

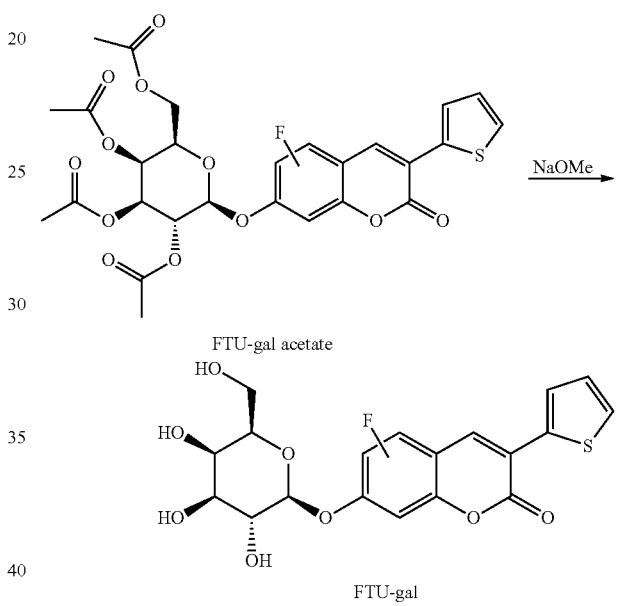

FTU-gal acetate

FTU-gal

A mixture was prepared by adding 1.2 grams of FTU-gal acetate from Example 6 to 15 mL of methanol. Most of the FTU-gal acetate dissolved. Complete dissolution occurred when 100 milligrams of NaOMe was added and a yellow color formed. The solution was stirred at room temperature under nitrogen for 1 to 2 hours with a yellow precipitate forming slowly. The solution was filtered and the yellow solid was dried on the filter. The yellow solid was then dissolved in about 500 mL of warm methanol and allowed to cool in a refrigerator, and then cooled further in a freezer (−20° C.) for three days.

A total of 0.58 grams was recovered in four fractions by successively filtering, reducing volume, and cooling in a refrigerator. The removal of acetate was confirmed by $^1$H NMR. The first fraction was determined by $^1$H and $^{19}$F NMR to have a mixture of 6-FTU-gal, 8-FTU-gal, and nonfluorinated products in a weight ratio of 0.69:0.03:0.28. The 6-FTU-gal appeared to come out of solution first, then the 8-FTU-gal, and then the non-fluorinated products.

Absorbance and emission spectra for the first fraction of FTU-gal was recorded at pH 2.5 to 8.0 in the presence and absence of β-D-galactosidase, and then compared to spectra of TU-gal (prepared according to U.S. Pat. No. 6,566,508 (Bentsen et al.) under the same conditions.

Figure 6:
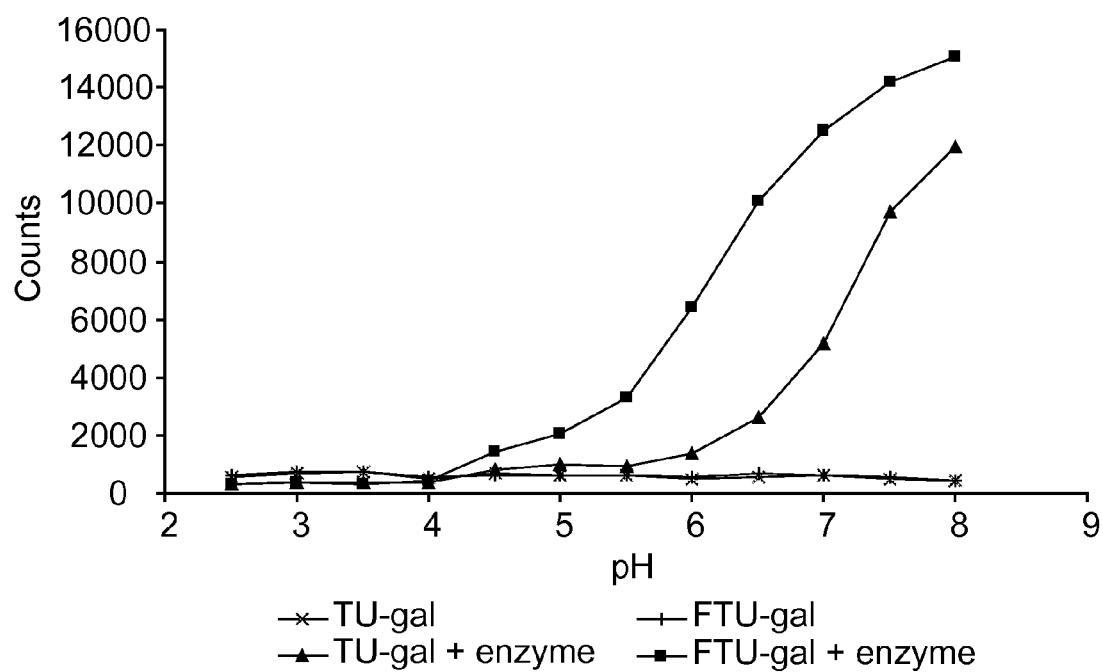
FIG. 6 shows emission at 495 nm (with excitation at 430 nm) for 3-thienylumbelliferone-pyanogalactoside (TU-gal), TU-gal+enzyme, fluorinated 3-thienylumbelliferone-pyanogalactoside (FTU-gal), and FTU-gal+enzyme as a function of pH.

Emission spectra (at 495 nm) were recorded at 430 nm excitation to minimize a noticeable absorption from the unreacted FTU-gal at the reacted anion maximum (405 nm), as seen in FIG. 6. The graph shows more than 2-fold enhancement in intensity from pH 5 to 7 versus TU that is not fluorinated. About two-thirds of the sample tested was fluorinated.

Example 8 and Comparative Example C1

Detection of Microbial Colonies

Preparation of a Bacterial Culture Plate

A mixture of 50 grams of xanthan gum powder and 50 grams of locust bean gum powder was placed in a 500 mL bottle and shaken manually for about 5 minutes. A cover film was prepared by sprinkling the mixture onto the adhesive of a pressure-sensitive adhesive coated sheet that is commercially available under the trade designation 9795R ADVANCED SEALING TAPE from 3M Company in St. Paul Minn. The adhesive coated sheet was tilted to remove excess powder. The coating weight of the gums was approximately 85 milligrams per 24 square inches (i.e, 0.55 milligrams per square centimeter).

A growth medium mixture was prepared by mixing 22.8 parts of pancreatic digest of casein, 15.9 parts of yeast extract, 45.5 parts of sodium pyruvate, 4.1 parts of dextrose, 9.0 parts of dibasic potassium phosphate, and 2.8 parts of monobasic potassium phosphate. A growth medium broth was prepared by mixing 500 mL of deionized water with 14.78 grams of the growth medium mixture in a beaker using an air motor mixer followed by adding 5 grams of locust bean gum in small increments, and mixing for several minutes. The beaker was covered with foil and the mixture was heated to 80° C., mixed for about 6 minutes, and then allowed to cool for about ten minutes while mixing without heat. The broth was then poured into a sterilized beaker, covered with a plastic bag and refrigerated. The cooled broth was stirred carefully with a spatula to avoid forming air bubbles and then knife coated onto a 24.4 cm wide sheet of 4 mil thick polyethylene terephthalate film that is commercially available under the trade designation MELINEX 453 from DuPont Teijin Films in Hopewell Va. The broth coated film was dried in an oven set at a temperature of 210° C. for about 10 minutes. The dried coating weight was about 1 mg per square centimeter.

A 20.3 centimeter (cm) wide sheet of 4 mil (a mil is equal to 0.001 inches) thick closed cell polystyrene foam (commercially available from American Fuji Seal, Inc. of Bardstown, Ky.) was laminated to a pressure-sensitive adhesive transfer tape on a release liner. The specific transfer tape used has an acrylic pressure-sensitive adhesive and is commercially available from 3M Company (Saint Paul, Minn.) under the trade designation 3M TRANSFER ADHESIVE 927. Circular discs measuring 5 cm in diameter were die-cut and removed from the laminate, forming circular openings centered within a 7.6 cm square from one end of 7.6 by 10.16 cm rectangle. The liner was removed and the adhesive-coated surface of the polystyrene foam was adhered to the broth coated film to provide a base member having a broth-coated self-supporting substrate and a hydrophobic spacer element (i.e., "foam dam") adhered to the broth-coated surface of the supporting substrate. Rectangular plates measuring 7.6 cm by 10.16 cm were cut from the laminate, with the circular openings centered within a 7.6 cm square on one end of the 10.16 cm length. The cover film was attached to the base member with the powder coated side facing the foam dam with a double sided pressure-sensitive adhesive tape to form a culture plate.

Preparation of Indicator Solutions

For Example 8, an indicator solution was prepared by dissolving FTU-gal from Example 6 in DMSO at a 50 mM (millimolar) concentration (Indicator 1). The solution was further diluted 20-fold to provide a 2.5 mM solution (Indicator 2).

For Comparative Example C1, indicator solutions were prepared by dissolving TU-gal in DMSO at a 20 mM concentration (Indicator 3). The solution was further diluted to provide a 2.5 mM solution (Indicator 4).

Preparation of Polymeric Particle Suspension

A suspension of 600 mg of acrylate particles (MX-180) in 12 mL of Butterfield's buffer, which can be obtained from 3M Company (Saint Paul, Minn.), was vortexed until homogeneous and then sonicated at 40° C. for 50 minutes.

Preparation of Bacterial Samples

A tryptic soy agar plate (commercially available under the trade designation BACTO Tryptic Soy Agar from Becton Dickinson in Sparks, Md.) was prepared at 3 wt percent according to the manufacturer's instructions. The plate was streaked with *Escherichia coli* (ATCC 29425 from The American Type Culture Collection in Manassas, Va.), and incubated overnight at 37° C. A colony isolated from the streak plate was inoculated into 9 mL of tryptic soy broth (commercially available under the trade designation BD BACTO Tryptic Soy Agar from Becton Dickinson in Sparks, Md.) and incubated at 37° C. overnight (18-20 hours). The resulting broth was diluted with Butterfield's Buffer to provide a bacterial suspension having an estimated $10^3$ organisms per mL.

Individual samples were prepared in ten 1.5 mL sterile eppendorf tubes having 1 mL of polymeric particle suspension in 6 of the tubes, and 1 mL of Butterfield's buffer in 4 of them. To each of the tubes, either 10 microliters of Indicator 2, Indicator 3, or Indicator 4, or 4 microliters of Indicator 1 was added, followed by adding 10 microliters of the $10^3$ *E. coli* suspensions to each tube. Table 1 summarizes Example 8-1 to 8-5 and Comparative Examples C1-C5. The Sample Indicator Concentration (Sample Concentration of Fluorogenci Compound) is in nanomolar concentration (nM) units.

A 1 mL sample was inoculated into a bacterial culture plate prepared as described above. The description of each sample is shown in Table 1.

TABLE 1

Composition of Examples 7-1 to 7-5 and Comparative Examples C-1 to C-5

| Example | Compound | Concentration of Fluorogenic Compound | Sample Concentration of Fluorogenic Compound | MX-180 particles |
|---|---|---|---|---|
| 8-1 | FTU-gal | 50 mM | 200 nM | Yes |
| 8-1 | FTU-gal | 50 mM | 200 nM | Yes |

TABLE 1-continued

Composition of Examples 7-1 to 7-5 and Comparative Examples C-1 to C-5

| Example | Compound | Concentration of Fluorogenic Compound | Sample Concentration of Fluorogenic Compound | MX-180 particles |
|---|---|---|---|---|
| 8-3 | FTU-gal | 2.5 mM | 25 nM | Yes |
| 8-4 | FTU-gal | 50 mM | 200 nM | No |
| 8-5 | FTU-gal | 2.5 mM | 25 nM | No |
| C-1 | TU-gal | 20 mM | 200 nM | Yes |
| C-2 | TU-gal | 20 mM | 200 nM | Yes |
| C-3 | TU-gal | 2.5 mM | 25 nM | Yes |
| C-4 | TU-gal | 20 mM | 200 nM | No |
| C-5 | TU-gal | 2.5 mM | 25 nM | No |

Plates 8-1 and C-1

Plates 8-1 and C-1 were incubated in an imaging/incubator system (In-vitro Imaging System FX Pro from Carestream Health in Rochester, N.Y.) that was set up to take 3 images every 2 hours. The first image was taken in white light, a second image under fluorescence conditions (emission at 420 nm with excitation at 535 nm) for 5 seconds, and a third under the same fluorescence conditions for 30 seconds. The temperature in the incubator varied from about 20° C. to 27° C.

Figure 7:
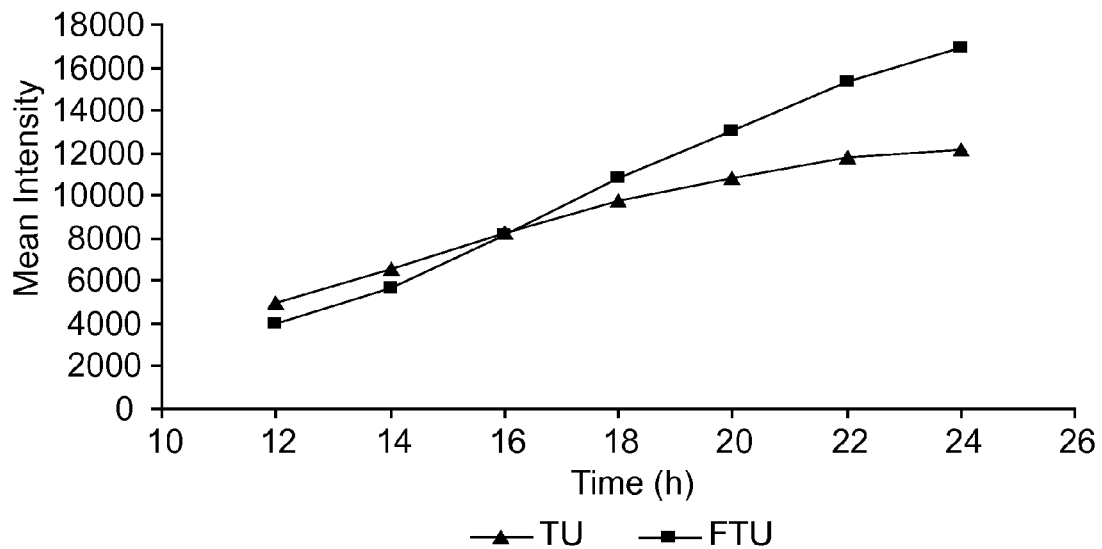
FIG. 7 shows the fluorescence of colonies as a function of time for 3-thienylumbelliferone (TU) and fluorinated 3-thienylumbelliferone (FTU).
Figure 8:
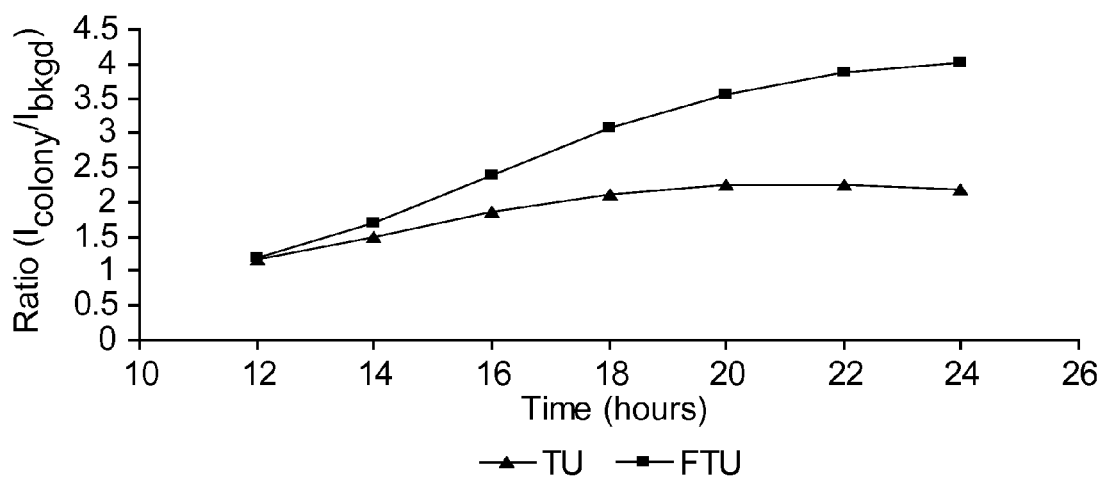
FIG. 8 shows the fluorescence of the colonies over the background noise as a function of time for TU and FTU.

Colonies were apparent in the images on Plates 8-1 and C-1 after 14 hours. The colonies appeared to exhibit similar intensities. Regions of interest were defined for 6 colonies and for 6 nearby spots of similar area without colonies to represent the background for each plate. The mean intensity for the defined areas (averaged across 6 colonies) was plotted against time for each plate at 30 seconds of fluorescent illumination as shown in FIG. 7. The plots show that fluorescence of FTU-gal containing samples and TU-gal containing samples were comparable at early stages; however, the fluorescence of the TU-gal containing samples tended to plateau over time while the fluorescence of FTU-gal containing samples continued to increase. This observation is consistent with the accumulation of acidic byproducts from bacterial metabolism reducing the emission from TU-gal containing sample relative to FTU-gal containing sample.

The data was normalized by averaging the signal from the six colonies and the six background spots and plotting the ratio of signal to background against time as seen in FIG. 7. The signal to noise (background) for the FTU-gal containing sample was always higher than for TU-gal containing sample and the difference increased with time.

Plates 8-2 to 8-5 and C-2 to C-5

Plates 8-2 to 8-5 and C-2 to C-5 were incubated at 30° C. The plates were removed from the incubator and imaged after 1 and 2 days. Images were recorded in a darkroom with a Canon 40D camera under 365 nm UV illumination. Colonies were visible on all plates, and were easier to see with the camera when the fluorophore was at lower concentrations (Plate 8-3 versus Plate 8-2 and Plate C-3 versus Plate C-2). The fluorescence from all colonies was much brighter in the presence of MX-180 particles than in those colonies without them.

Thus, embodiments of fluorogenic compounds, fluorophoric compounds, articles containing these compounds, and methods of detecting microorganisms using these compounds, and method of making these compounds are disclosed. One skilled in the art will appreciate that the present disclosure can be practiced with embodiments other than those disclosed. The disclosed embodiments are presented for purposes of illustration and not limitation, and the present disclosure is limited only by the claims that follow.

What is claimed is:

1. A compound of Formula (I)

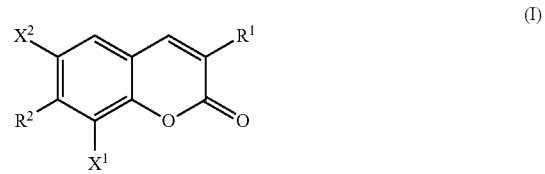

wherein
$R^1$ is —(CO)—$OR^3$, —(CO)—$NR^4R^5$, heterocyclic group, aryl, aralkyl, or cyano;
$R^2$ is an enzyme-labile group;
$R^3$ is alkyl, alkenyl, aryl, or aralkyl;
$R^4$ and $R^5$ are each independently hydrogen, alkyl, aryl, or aralkyl; and
either (a) $X^1$ is hydrogen and $X^2$ is fluoro or (b) $X^1$ is fluoro and $X^2$ is hydrogen, and wherein $R^2$ is a sugar group, sugar acid group, amino sugar group, carboxyl-terminated amino acid group, carboxyl-terminated peptide group, ester group, ester-containing group, phosphate group, or sulfate group; and wherein either
$R^2$ is a sugar group that is a monosaccharide group or a disaccharide group, or
$R^1$ is —(CO)—$OR^3$ where $R^3$ is alkyl, or
$R^2$ is a sugar group that is a monosaccharide group or a disaccharide group and $R^1$ is —(CO)—$OR^3$ where $R^3$ is alkyl.

2. The compound of claim 1, wherein $R^2$ is a sugar group that is a monosaccharide group or disaccharide group.

3. The compound of claim 1, wherein $R^1$ is —(CO)—$OR^3$ where $R^3$ is an alkyl.

4. The compound of claim 1, wherein $R^1$ is a heterocyclic group having a five-member heterocyclic ring.

5. The compound of claim 1, wherein $R^1$ is a heterocyclic group having a five-member heterocyclic ring fused to a benzene ring.

6. A composition comprising a mixture of a compound of Formula (I-1) and a compound of Formula (I-2);

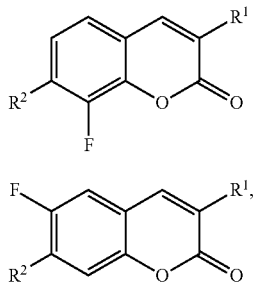

wherein
R¹ is —(CO)—OR³, —(CO)—NR⁴R⁵, heterocyclic group, aryl, aralkyl, or cyano;
R² is hydroxyl or an enzyme-labile group;
R³ is alkyl, alkenyl, aryl, or aralkyl; and
R⁴ and R⁵ are each independently hydrogen, alkyl, aryl, or aralkyl.

7. An article comprising:
a) a first layer that is a support layer;
b) a second layer adjacent to the support layer, wherein the second layer comprises a compound of Formula (I) according to claim 1.

8. The article of claim 7, wherein the second layer comprises a mixture of a compound of Formula (I-1) and a compound of Formula (I-2)

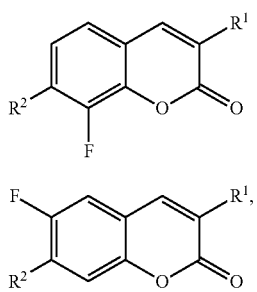

wherein
R¹ is —(CO)—OR³, —(CO)—NR⁴R⁵, heterocyclic group, aryl, aralkyl, or cyano;
R² is hydroxyl or an enzyme-labile group;
R³ is alkyl, alkenyl, aryl, or aralkyl; and
R⁴ and R⁵ are each independently hydrogen, alkyl, aryl, or aralkyl.

9. The article of claim 7, wherein the second layer further comprises a gelling agent, growth medium, or a combination thereof.

10. The article of claim 7, wherein the second layer is dehydrated.

11. The article claim 7, wherein the second layer further comprises polymeric particles.

12. The article of claim 11, wherein the polymeric particles comprise an acrylate polymer or copolymer, styrene polymer or copolymer, cellulosic polymer or copolymer, dextran polymer or copolymer, derivatives thereof, or combinations thereof.

13. The article of claim 11, wherein the polymeric particles have an average particle diameter in a range of 0.01 micrometers to 1 micrometer.

14. A method of detecting a microorganism, the method comprising:
providing a compound of Formula (I) according to claim 1; and
incubating a test sample with the compound of Formula (I), wherein the test sample contains an enzyme that cleaves the R² group of compound of Formula (I), resulting in the formation of a fluorophoric compound of Formula (Ib); and

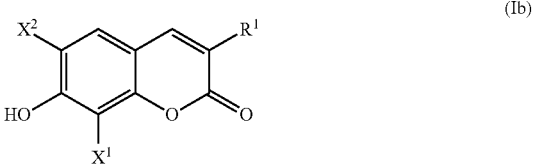

exciting the fluorophoric compound of Formula (Ib) with a first wavelength of light and detecting light emitted at a second wavelength of light that is longer than first wavelength of light.

15. The method of claim 14, wherein the step of incubating the test sample with the fluorogenic compound comprises adding the test sample in a liquid form to a dehydrated layer containing the fluorogenic compound of Formula (Ia) and a growth medium.

16. The method of claim 14, wherein the method further comprises sequestering the compound of Formula (Ib) on polymeric particles.

17. The method of claim 16, wherein the polymeric particles have an average particle diameter in a range of 0.01 micrometers to 1 micrometer.

* * * * *

UNITED STATES PATENT AND TRADEMARK OFFICE
CERTIFICATE OF CORRECTION

Page 1 of 2

PATENT NO. : 9,434,975 B2
APPLICATION NO. : 14/008905
DATED : September 6, 2016
INVENTOR(S) : Stephen B. Roscoe et al.

It is certified that error appears in the above-identified patent and that said Letters Patent is hereby corrected as shown below:

On the Title Page

Column 2 (Other Publications)
Line 24, delete "Chemcials," and insert -- Chemicals, --, therefor.
Line 31, delete "Phosphtase" and insert -- Phosphatase --, therefor.

Column 2 (Attorney, Agent, or Firm)
Line 2, delete "Silverman" and insert -- Silverman, Ph.D. --, therefor.

In the Specification

Column 1
Line 8, after "U.S.C." insert -- § --.

Column 12
Line 50-51, delete "diazobicyclo" and insert -- diazabicyclo --, therefor.

Column 19
Line 14, delete "carageenan," and insert -- carrageenan, --, therefor.
Line 25-26, delete "polyalkyene" and insert -- polyalkylene --, therefor.

Column 22
Line 53, delete "Acenitobacter" and insert -- Acinetobacter --, therefor.
Line 67, delete "pudita)," and insert -- putida), --, therefor.

Column 38
Line 53, delete "Fluorogenci" and insert -- Fluorogenic --, therefor.

Signed and Sealed this
Fourteenth Day of November, 2017

Joseph Matal
*Performing the Functions and Duties of the
Under Secretary of Commerce for Intellectual Property and
Director of the United States Patent and Trademark Office*

In the Claims

Column 40
Line 48 (approx.), in Claim 1, delete "monosaccaride" and insert -- monosaccharide --, therefor.
Line 52 (approx.), in Claim 1, delete "monosaccaride" and insert -- monosaccharide --, therefor.

Column 41
Line 38 (approx.), in Claim 8, delete "(I-2))" and insert -- (I-2) --, therefor.